US010258293B2

(12) United States Patent
Carlsgaard et al.

(10) Patent No.: US 10,258,293 B2
(45) Date of Patent: Apr. 16, 2019

(54) USER INTERFACE FEATURES FOR A DIABETES MANAGEMENT APPLICATION

(75) Inventors: Eric S. Carlsgaard, Zionsville, IN (US); Mark G. Mears, Westfield, IN (US); Robert E. Reinke, Indianapolis, IN (US); Justin David Adams, Noblesville, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 647 days.

(21) Appl. No.: 13/462,055

(22) Filed: May 2, 2012

(65) Prior Publication Data
US 2013/0172706 A1    Jul. 4, 2013

Related U.S. Application Data

(60) Provisional application No. 61/581,159, filed on Dec. 29, 2011, provisional application No. 61/581,331, filed on Dec. 29, 2011.

(51) Int. Cl.
*A61B 5/00* (2006.01)
*G06Q 10/10* (2012.01)
(Continued)

(52) U.S. Cl.
CPC ............ *A61B 5/743* (2013.01); *A61B 5/7275* (2013.01); *G06Q 10/1093* (2013.01); *G16H 10/60* (2018.01); *G16H 50/20* (2018.01)

(58) Field of Classification Search
None
See application file for complete search history.

(56) References Cited

U.S. PATENT DOCUMENTS 7,291,107 B2    11/2007  Hellwig et al.
7,553,281 B2     6/2009  Hellwig et al.
(Continued)

FOREIGN PATENT DOCUMENTS

CN    1701335 A    11/2005
CN  102265279 A    11/2011
(Continued)

OTHER PUBLICATIONS

Smiths Medical MD, Inc., Deltec Cozmo®, Fine Tuning Your Deltec Cozmo® Insulin Pump Settings, Overnight Basal Rate Test Instructions, 2 pp, Date Unknown.
(Continued)

*Primary Examiner* — Elaine Gort
*Assistant Examiner* — Rachelle L Reichert
(74) *Attorney, Agent, or Firm* — Harness, Dickey & Pierce, P.L.C.

(57) ABSTRACT

A method is provided for contextualizing manual entries of blood glucose measures for a patient into a patient log of a portable computing device. The method includes: administering a structured collection procedure, where the structured collection procedure specifies two or more collection actions for obtaining blood glucose measures from a patient; generating a reminder notification for a given collection action of the structured collection procedure, where the given collection action is associated with a given event of patient; and displaying a data entry interface upon receipt of an acceptance input from a user in response to the reminder notification, where the data entry interface includes a first input for a blood glucose measure and a second input for an event associated with the blood glucose measure, such that value for the second input is defaulted to the given event from the reminder notification.

15 Claims, 18 Drawing Sheets

(51) Int. Cl.
*G16H 10/60* (2018.01)
*G16H 50/20* (2018.01)

(56) References Cited

U.S. PATENT DOCUMENTS

| | | |
|---|---|---|
| 2002/0072858 A1 | 6/2002 | Cheng |
| 2004/0172284 A1 | 9/2004 | Sullivan et al. |
| 2006/0036134 A1* | 2/2006 | Tarassenko et al. ......... 600/300 |
| 2006/0047192 A1 | 3/2006 | Hellwig et al. |
| 2006/0137695 A1 | 6/2006 | Hellwig et al. |
| 2007/0128682 A1* | 6/2007 | Rosman ............. G06F 19/3437 435/14 |
| 2007/0230282 A1 | 10/2007 | May et al. |
| 2008/0058628 A1 | 3/2008 | Hellwig et al. |
| 2008/0177149 A1* | 7/2008 | Weinert ............... G06F 19/322 600/300 |
| 2008/0234943 A1 | 9/2008 | Ray et al. |
| 2008/0287922 A1 | 11/2008 | Panduro |
| 2009/0036828 A1* | 2/2009 | Hansen et al. .................. 604/66 |
| 2010/0016700 A1 | 1/2010 | Sieh et al. |
| 2010/0069730 A1 | 3/2010 | Bergstrom |
| 2010/0160757 A1 | 6/2010 | Weinert et al. |
| 2010/0160759 A1 | 6/2010 | Celentano et al. |
| 2010/0168660 A1 | 7/2010 | Galley et al. |
| 2010/0198142 A1 | 8/2010 | Sloan et al. |
| 2010/0212675 A1 | 8/2010 | Walling et al. |
| 2010/0218132 A1* | 8/2010 | Soni .................... G06F 19/3406 715/771 |
| 2010/0331650 A1 | 12/2010 | Batman |
| 2011/0029870 A1 | 2/2011 | May et al. |
| 2011/0237918 A1 | 9/2011 | Wagner et al. |
| 2012/0242482 A1 | 9/2012 | Elumalai et al. |

FOREIGN PATENT DOCUMENTS

| | | |
|---|---|---|
| EP | 2367146 | 9/2011 |
| WO | 2010/089304 | 8/2010 |

OTHER PUBLICATIONS

Smiths Medical MD, Inc., Deltec Cozmo®, User Manual, Deltec Cozmo® Insulin Pump, 245 pp, Date Unknown.
"Glooko App Offers Diabetics Easier Self-Checks", www.phys.org/news/2011-11-glooko-app-diabetics-easier-self-checks.html; (2011).
Glooko Logbook & MeterSync Cable, www.glooko.com/product/logbook, (2011).
UILocalNotification Class Reference, iOS Developer Library, (2010), pp. 1-13, XP055091111 (url:https://developer.apple.com/Library/ios/documentation/iPhone/Reference/UILocalNotification_Class/UILocalNotification_Class.pdf).

* cited by examiner

USER INTERFACE FEATURES FOR A DIABETES MANAGEMENT APPLICATION

CROSS-REFERENCE TO RELATED APPLICATIONS

This application claims the benefit of U.S. Provisional Application No. 61/581,159, filed on Dec. 29, 2011 and 61/581,331, filed on Dec. 29, 2011. The entire disclosures of the above applications are incorporated herein by reference.

FIELD

The present disclosure relates to a diabetes management application that manages manual data entries received from a patient and enhanced user interface features implemented by the diabetes management application.

BACKGROUND

For people with diabetes, successful management requires monitoring the effects lifestyle changes can have in both the short term and long term. Regular testing of blood glucose level (bG) is an important way to monitor such effects over shorter time frames. Portable handheld glucose meters and associated test strips have been used for years in both homes and healthcare facilities to obtain blood glucose values.

Patients and healthcare professionals may thereby track and analyze glucose measurements over a period of time to assess changes in the patient over the course of a day, week, or other desirable timeframe. For example, some healthcare professionals may instruct a patient to obtain glucose measurements seven or more times a day over a course of a few consecutive days so that patients may observe the changes associated with particular events or times of day. Structured test procedures are typically administered in an automated manner by the glucose meter. During testing, the patient is prompted to input blood samples into the glucose meter at designated times in accordance with a structured test procedure. Glucose measures derived from the blood samples are in turn properly tagged and associated with the structured test procedure being administered by the glucose meter.

More recently, diabetes management applications have been developed for use, independent from a glucose meter. For example, a diabetes management application may reside on a patient's phone or another type of mobile computing device. Such diabetes management applications can likewise help the patient manage structured test procedures by reminding them to collect blood glucose measures and ensuring that the collected values obey certain constraints. Unlike glucose meters, glucose measures are input manually by the patient into the diabetes management application. Accordingly, there is a need to properly manage manual data entries received from the patient in relation to the structured test being administered to the patient. There is also a need to develop enhanced user interface features to facilitate capturing and managing the manual data entries provided by the patient.

This section provides background information related to the present disclosure which is not necessarily prior art.

SUMMARY

In one aspect of the present disclosure, a computer-implemented method is provided for contextualizing manual entries of blood glucose measures for a patient into a patient log of a portable computing device. The method includes: administering a structured collection procedure, where the structured collection procedure specifies two or more collection actions for obtaining blood glucose measures from a patient; generating a reminder notification for a given collection action of the structured collection procedure, where the given collection action is associated with a given event of patient; and displaying a data entry interface upon receipt of an acceptance input from a user in response to the reminder notification, where the data entry interface includes a first input for a blood glucose measure and a second input for an event associated with the blood glucose measure, such that value for the second input is defaulted to the given event from the reminder notification.

The method further includes: receiving an expected time for the given event from the user; creating a reminder event for the given collection action in a calendar application, where the reminder event is calculated from the expected time for the given event and specifies a time at which to initiate a reminder notification; and generating the reminder notification for the given collection action in accordance with the reminder event in the calendar application. Each collection action of the structured collection procedure is associated an event type and the event type may be selected from the group consisting of meal, sleep, exercise, fasting and insulin intake.

In another aspect, the data entry interface further includes a status selection bar having a slide-able indicator, wherein the status selection bar represents a range of values for blood glucose measures and the indicator is slide-able along the status selection bar to select a value for a blood glucose measure. The status bar has a graduated color scheme such that each color represents a sub-range of values for blood glucose measures.

In yet another aspect of the present disclosure, a computer-implemented method for displaying results of an n-day patient profile to a user of a portable computing device. The method includes: administering a structured collection procedure over a period of n days, where the structured collection procedure specifies a plurality of predefined time slots for obtaining blood glucose measures from a patient throughout the course of a given day; determining an orientation of a display of the computing device; displaying a first graph for the structured collection procedure when a longitudinal axis of the display is orientated vertical, the first graph plots blood glucose measures from each of the n days on the first graph such that one axis of the first graph represents time during a single day and blood glucose measures from different days overlay each other on the first graph; and displaying a second graph for the structured collection procedure when the longitudinal axis of the display is orientated horizontal, the second graph plots blood glucose measures for each of the n days along one axis of the second graph that represents time over the course of n days.

On either graph, the range of acceptable blood glucose measures may be demarcated with visual indicia on at least one of the first graph and the second graph. In addition, blood glucose measures from different days may be plotted with different visual indicia, such as color, on at least one of the first graph and the second graph.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

Figure 1:
FIG. 1 is a drawing depicting a patient and a treating clinician.

The drawings described herein are for illustrative purposes only of selected embodiments and not all possible implementations, and are not intended to limits the scope of the present disclosure. Corresponding reference numerals indicate corresponding parts throughout the several views of the drawings.

DETAILED DESCRIPTION

FIG. 1 depicts a person 100 with diabetes and a healthcare professional 102 in a clinical environment. Persons with diabetes include persons with metabolic syndrome, pre-diabetes, type 1 diabetics, type 2 diabetics and gestational diabetics and are collectively referred to as a patient. Healthcare providers for diabetes are diverse and include nurses, nurse practitioners, physicians, and endocrinologists and are collectively referred to as a clinician. While this disclosure makes reference to diabetes care, it is readily understood that the concepts related to diabetes care can be applied to other types of chronic diseases. For example, this disclosure makes reference to blood glucose measures but the concepts are extendable to other types of biomarkers of a patient including but not limited to an interstitial glucose value, an HbA1c value, a heart rate measurement, a blood pressure measurement, lipids, triglycerides, cholesterol and the like.

During a healthcare consultation, the patient 100 typically shares with the clinician 102 a variety of patient data including blood glucose measurements, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. In some instances, patient data can be recorded manually or electronically by the patient 100 using a diabetes management application accessible on a handheld portable computing device 104. An exemplary diabetes management application is further described below. The clinician 102 will then analyze the patient data. After analyzing the patient data and reviewing adherence of the patient 100 to previously prescribed therapy, the clinician 102 can decide whether to modify the therapy for the patient 100.

Figure 2:
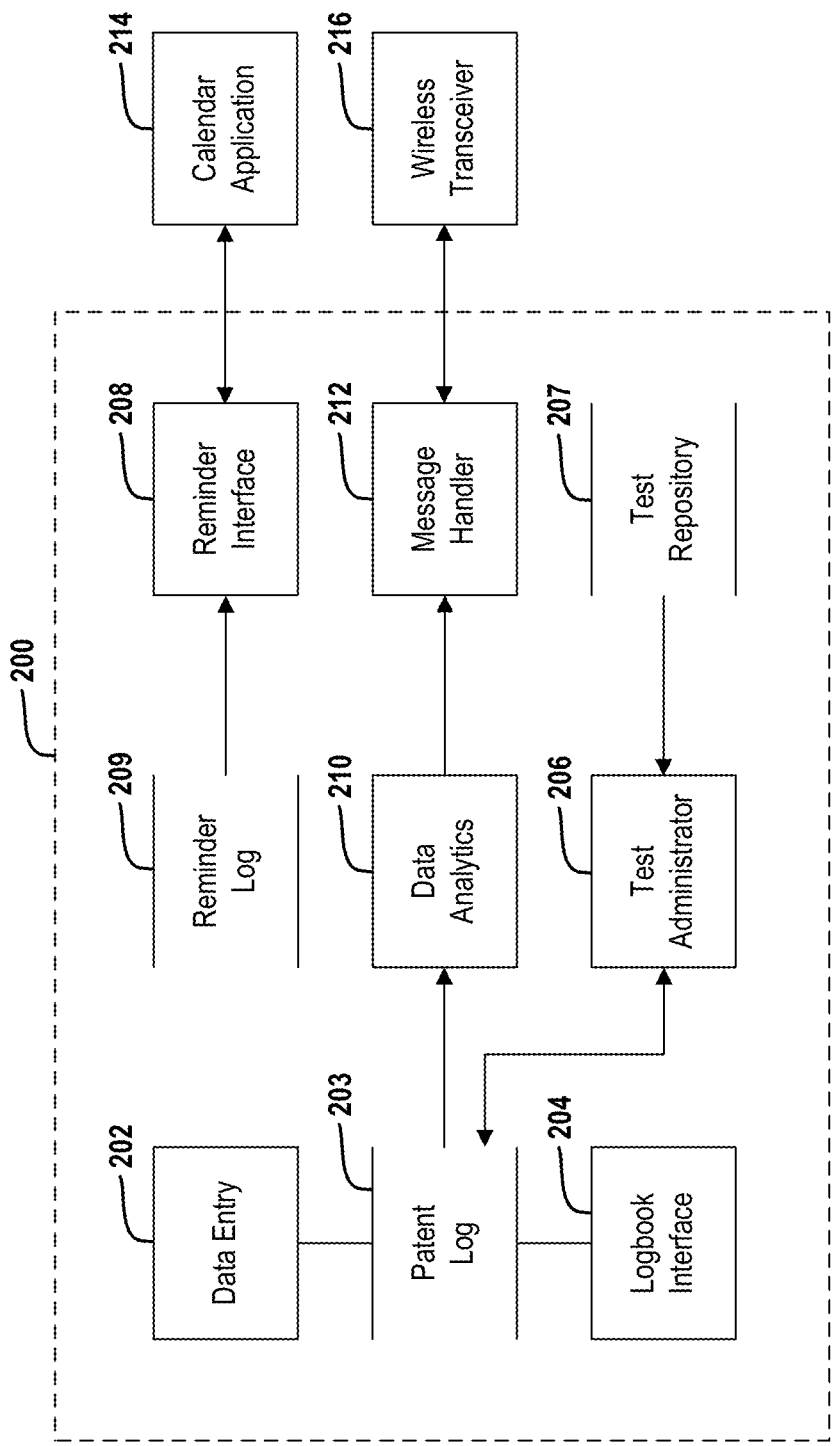
FIG. 2 is a block diagram of an exemplary diabetes management application 200 which may reside on a portable computing device.

FIG. 2 depicts an exemplary diabetes management software application 200 which may be implemented on a portable computing device, such a mobile phone. The diabetes management application 200 is intended for use by persons with diabetes. Generally, the diabetes management application 200 will support entry, storage, analysis, display and transfer of blood glucose measures and other health indicators. The diabetes management application 200 will also provide structured collections procedures to help the user increase their understanding of how to manage their diabetes. Because people tend to carry their portable computing device (e.g., phone) with them, the diabetes management application 200 will provide persons with diabetes an easy-to-use way to capture and track their health information. Further details regarding an exemplary diabetes management application 200 may be found in U.S. patent application Ser. No. 13/461,974 entitled "Diabetes Management Application for Mobile Phone" which is filed concurrently herewith and incorporated herein by reference.

In an exemplary embodiment, the diabetes management application 200 may include a data logging module 202, a logbook management module 204, a test administration module 206, a reminder interface module 208, a data analytics module 210 and a message handler 212. Each of these components is further described below. It is understood that components relevant to this disclosure are discussed herein, but that other components may be needed to implement the diabetes management application.

Figure 3A:
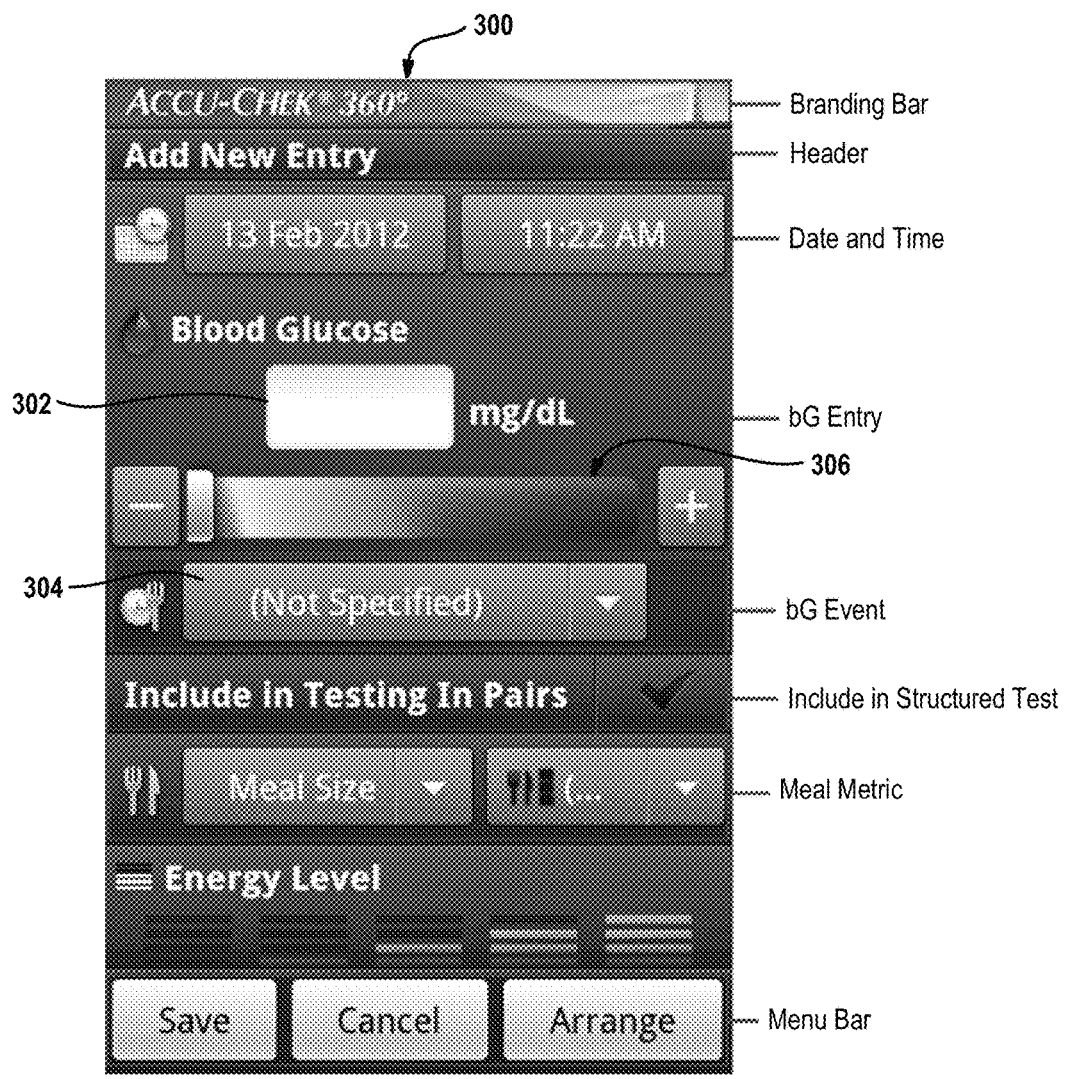
FIGS. 3A-3C illustrate an exemplary user interface for the inputting data entries.
Figure 3B:
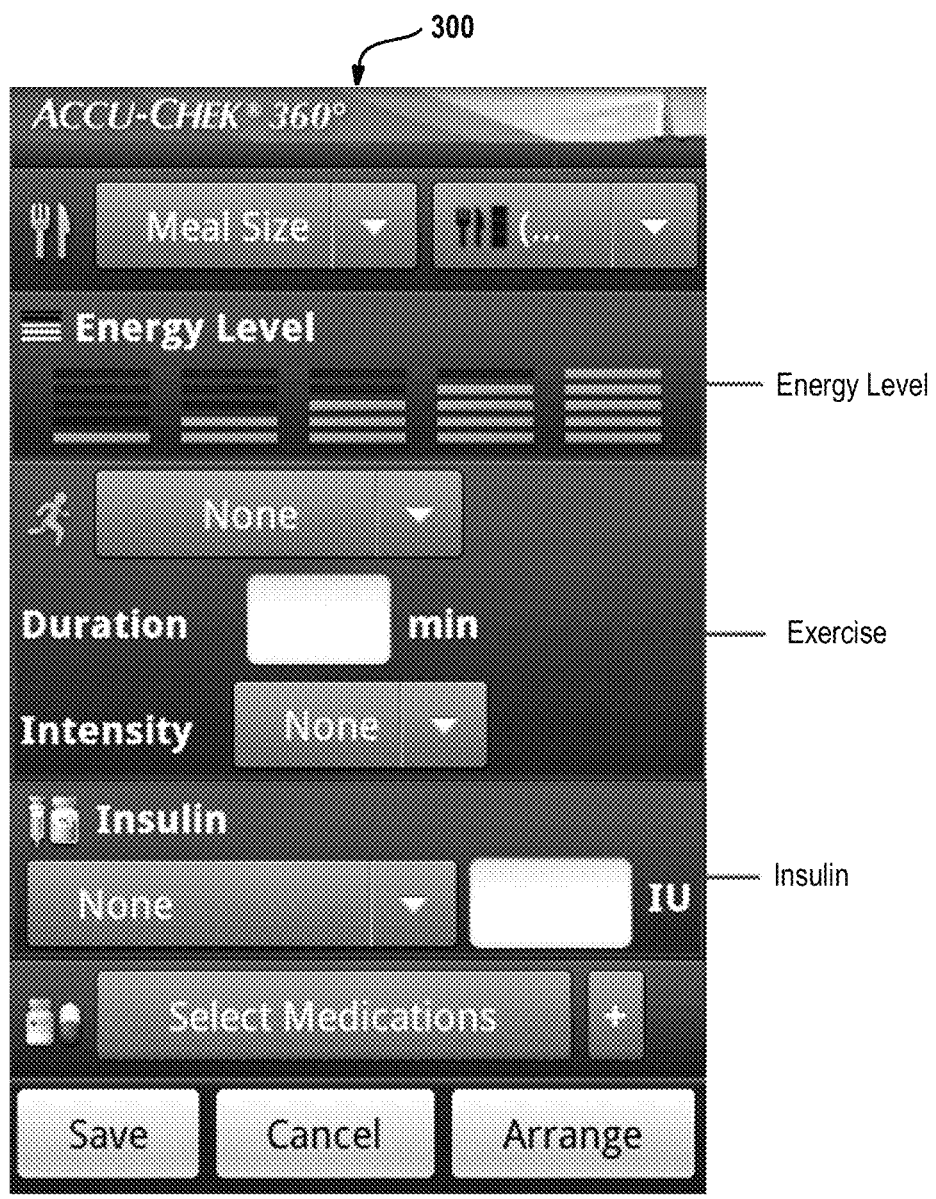
Figure 3C:
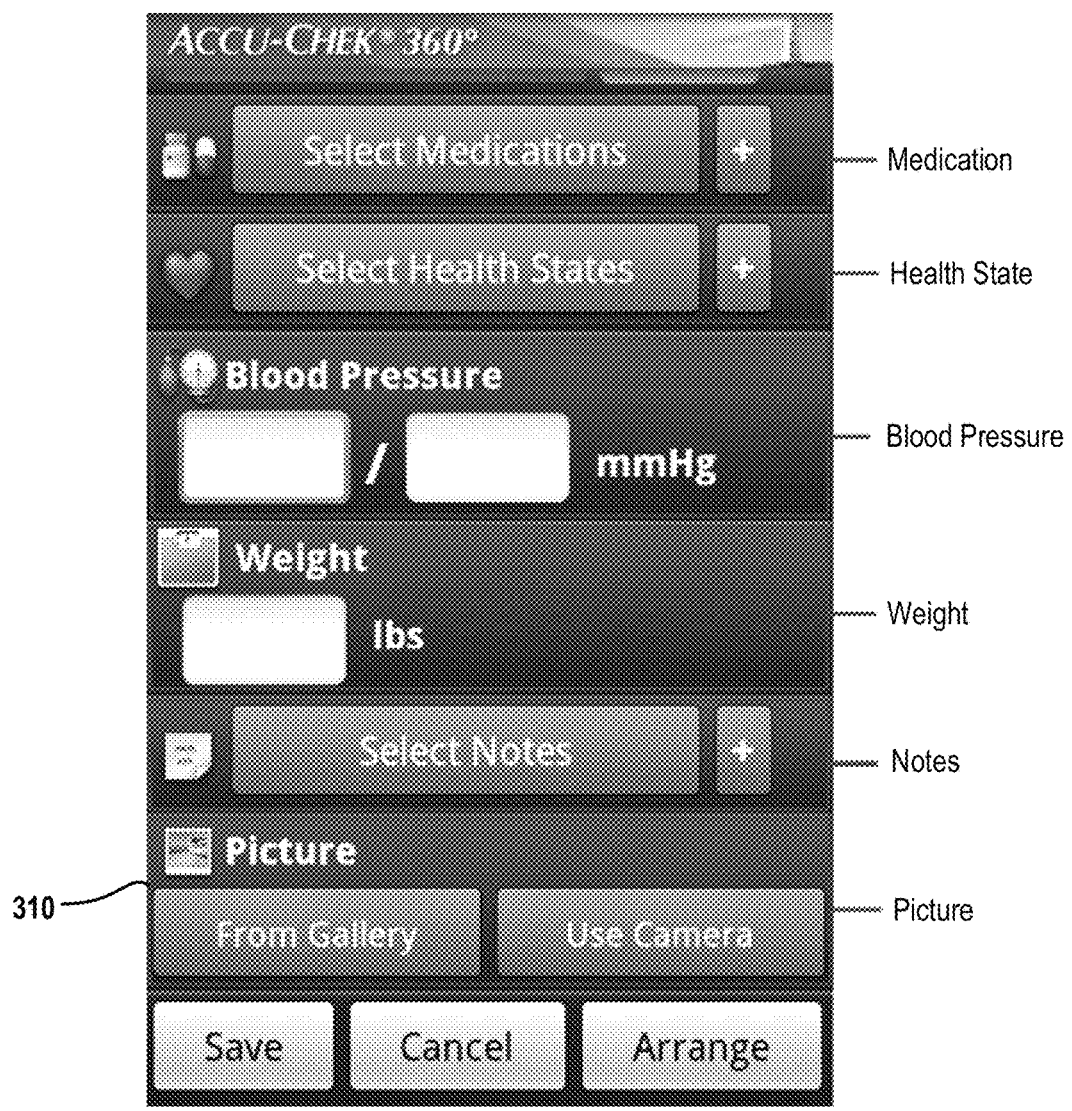

The data logging module 202 provides the capability to manage records in a patient log 203 residing on the device. An exemplary user interface 300 for adding records to the patient log is shown in FIGS. 3A-3C. Each record contains data pertaining to a patient's health. In the case of diabetes care, each record preferably includes a blood glucose measure of the patient. Logbook records may further include data pertaining to a patient's insulin intake, food intake, exercise, energy level, blood pressure, weight and other physiological metrics. Of note, the data entry interface further includes an input at 310 for associating an image file with the data entry. This input may be used, for example, to take a picture of a meal associated with the blood glucose measure. The image file can then be stored with the data entry and subsequently reviewed, for example, by an attending physician. It is envisioned that other media, such as a video or a voice note, may be associated with the data entry. Likewise, it is envisioned that other types of supplemental information, for example, geolocation from a GPS device or temperature, altitude or humidity measures from a suitable sensor, may also be associated without user intervention with the data entry. In addition, the data logging module enables a user to edit, delete or otherwise manage records in the patient log.

Figure 4A:
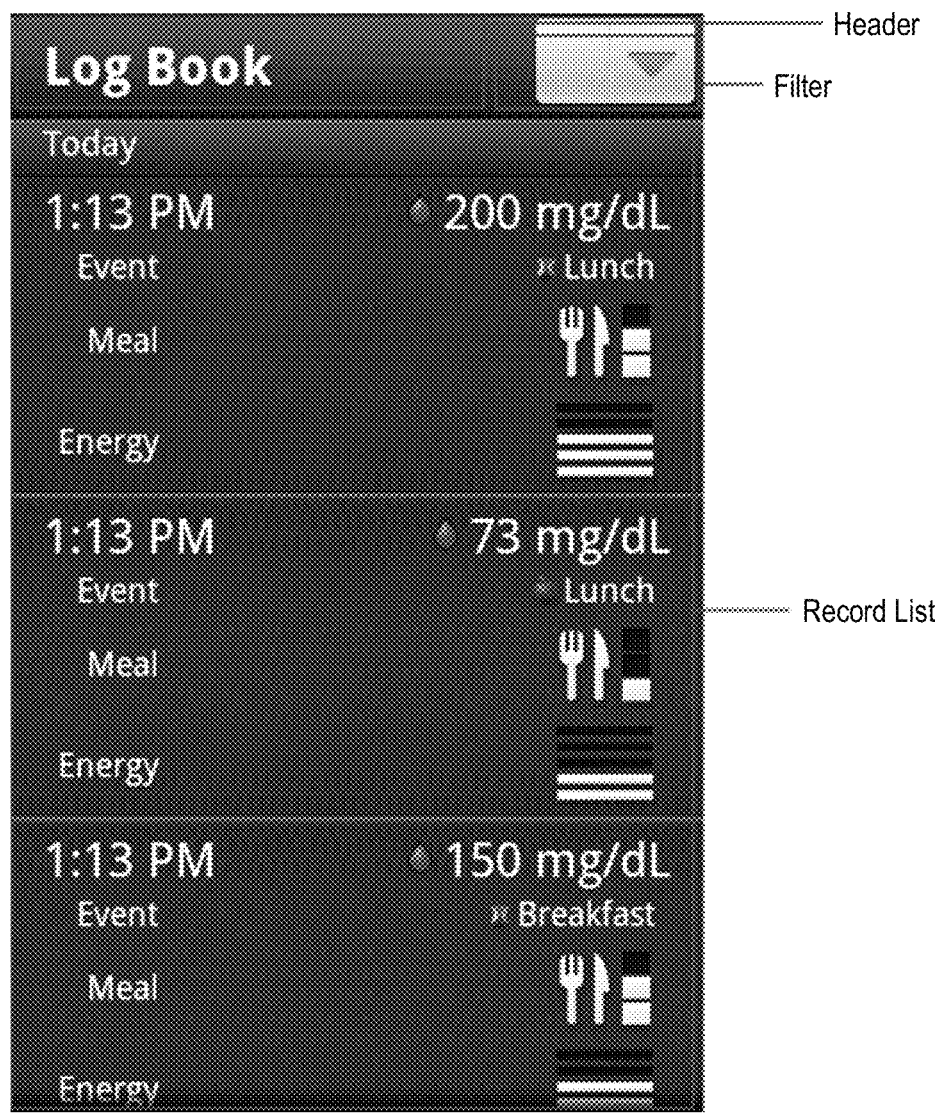
FIGS. 4A and 4B illustrate exemplary user interfaces for viewing entries in the patient log.
Figure 4B:

The logbook management module 204 provides an interface for displaying logbook records on a display of the device. In one embodiment, the logbook management module 204 enables the user to view logbook entries, for example, in a listing as shown in FIG. 4A. By selecting a given entry in the listing, the user is provided a more detailed view of the given entry as shown in FIG. 4B. The logbook management module 204 may also support other report formats. For example, the user may select to view a trend report. In other examples, the user may select to view a report associated with a structured collection procedure, such as a three day profile report or a testing in pairs report, as will be further described below. The logbook management module 204 may also provide the capability to export logbook data into a data file having a particular data format, such as an eXtensible Markup Language (XML) file. It is envisioned that the logbook management module may support other types of data formats and/or report formats.

The test administration module 206 administers or manages a structured collection procedure. A structured collection procedure specifies one or more collection actions for obtaining glucose measures from the patient (also referred to as a structured test). Unlike conventional glucose meters, glucose measures are input manually by the patient into the data logging module 202 of the diabetes management application 200. Accordingly, there is a need to properly manage manual data entries received from the patient in relation to the structured collection procedure being administered to the patient. Techniques for managing manual data entries are described in detail below.

For illustration purposes, the diabetes management application 200 supports two exemplary structured tests: the three-day profile structured test and the testing in pairs (TiP) structured test. The three-day profile tests involve obtaining blood glucose measures at predefined time slots throughout the course of a given day and repeating the measures over a three day period. For example, the three-day profile test specifies obtaining blood glucose measures at seven different times during the day: pre-breakfast; post-breakfast; pre-lunch; post-lunch; pre-dinner; post-dinner; and bedtime. On the other hand, the testing in pairs test involves obtaining a pair of blood glucose measures in relation to a given event, such as a meal. Specifically, the pair of blood glucose measures for a given test should fall within a window of time which encapsulates the given event, such that a first measure occurs before the given event and the second measure occurs after the given event. Paired testing can address scenarios such as the relationship between portion sizes and postprandial glucose values, the effect of exercise on blood glucose control and the efficacy of insulin doses. While reference is made throughout this disclosure to these two particular structured tests, it is readily understood that the concepts disclosed herein are extendable to other types of structured tests.

The reminder module 208 provides an interface for configuring reminders. In an exemplary embodiment, the reminder module 208 interacts with a calendar application 214 on the device to implement reminders. More specifically, the reminder module 208 can create a reminder event for a particular action and log the reminder event with the calendar application 214. A reminder notification for the user can then be initiated by the calendar application 214 in accordance with the reminder event. The reminder module 208 also enables the user to manage various attributes associated with a reminder event, such as an occurrence time, recurrence, notification method, etc. The reminder module 208 can also provide additional functionality not supported by a conventional calendar application. For example, special reminder functions related to structure collection procedures are handled by the reminder module as will be further described below.

The data analytics module 210 facilitates reporting a patient data captured by the diabetes management application and stored in the patient log. The data analytics module 210 can selectively operate to analyze patient data and formulate reports regarding the same. For example, the data analytics module 210 can report blood glucose measures that fall within a defined time period (e.g., within 24 hours or the last week). In another example, the data analytics module 210 can report results from one or more completed structured collection procedures. Other types of reporting criteria may be implemented by the data analytics module.

Figure 5:
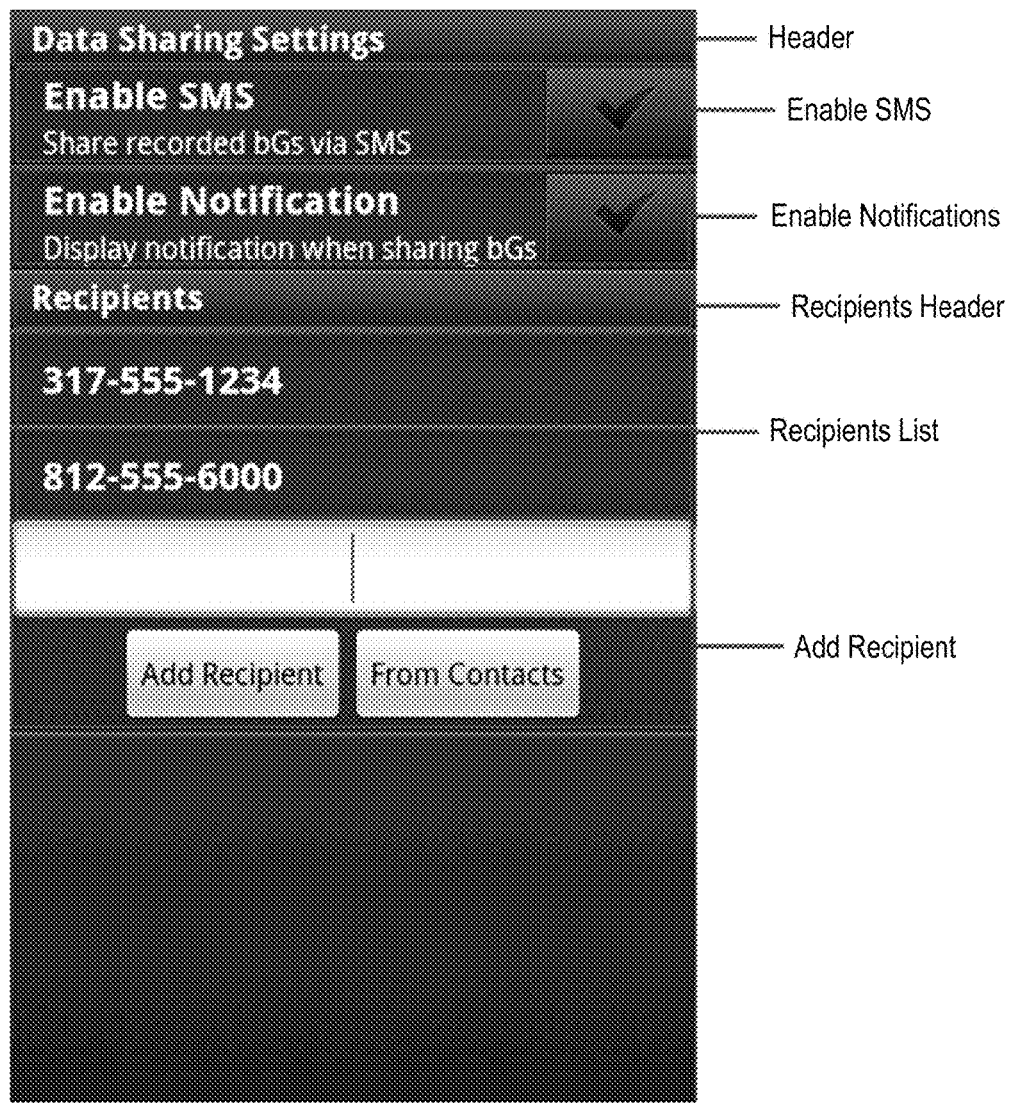
FIG. 5 illustrates an exemplary user interface for configuring settings for sharing patient data.

The data analytics module 210 interfaces with the message handler 212 to report patient data. The message handler 212 enables the user to configure settings for sharing patient data with others. FIG. 5 illustrates an exemplary user interface for configuring sharing setting. In this example, the user can specify the mechanism to share the patient data (e.g., email or text message) as well as a listing of recipients. The message handler in turn interacts with an appropriate wireless transceiver or network interface to transmit the report to the designated recipients.

Figure 6:
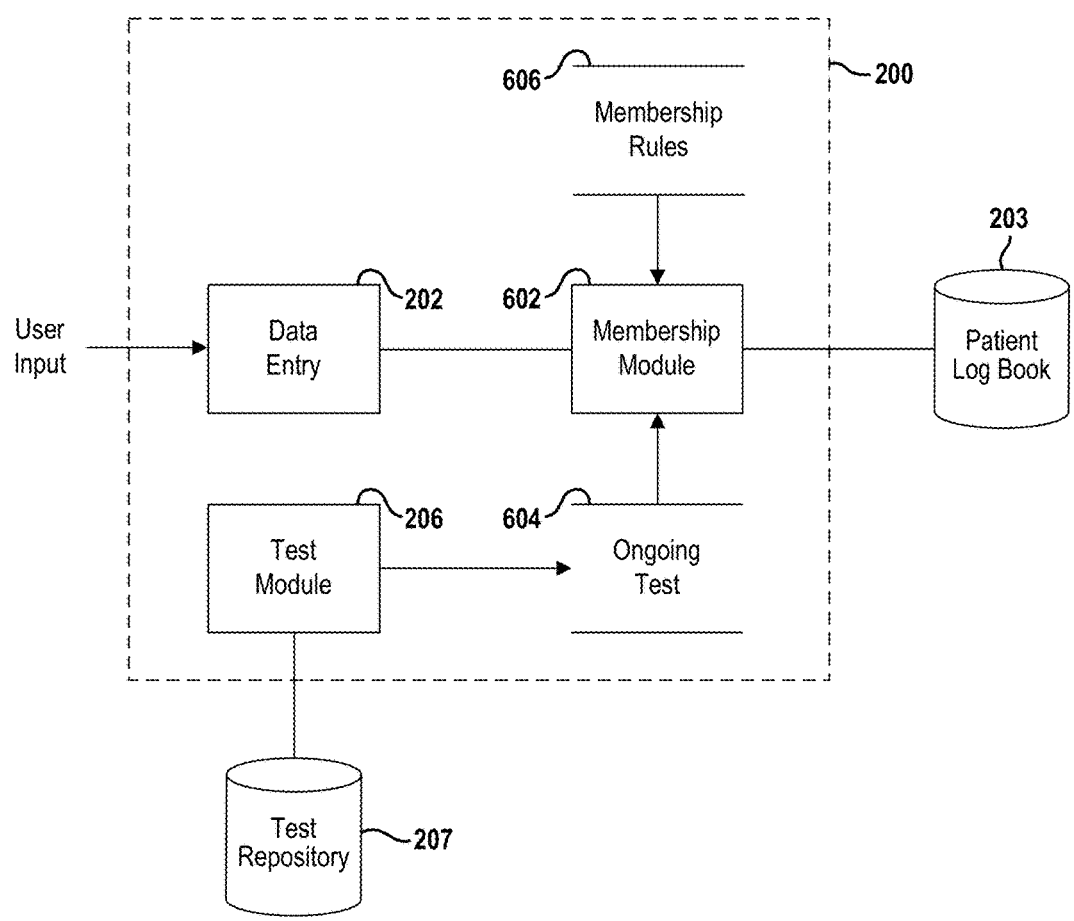
FIG. 6 is a block diagram depicting portions of the diabetes management application.

With reference to FIG. 6, exemplary techniques for managing manual data entries of blood glucose measures are described. For simplicity of the explanation set forth below, only one structured test is managed at any given time by the test administration module 206 although it is envisioned that other embodiments could support management of more than one structured test. In any case, the structured tests accessible to the test administration module 206 are stored in test repository 207 (i.e., data store) residing on the portable computing device. In addition to the data logging module 202 and the test administration module 206, the diabetes management application 200 may further include a membership module 602.

During administration of a given structure test, the data logging module 202 is configured to receive data entries from a user of the computing device. For example, a data entry may be for a blood glucose measure taken by the user, where the data entry includes a blood glucose measure along with a date and time at which the blood glucose measure was taken. It is readily understood that the data entry may further include other data related to the blood glucose measure and/or the patient. In other examples, a data entry may not include a blood glucose measure. Rather, the data entry may pertain to a meal event, an exercise event or other types of events or health parameters related to the patient (also referred to herein as non-blood glucose entries). In any case, one or more parameters of the data entry are input manually by the user of the computing device.

The membership module 602 is configured to receive the data entries from the data logging module 202 and evaluates the data entries for association with the structured test procedure currently being managed by the test administration module 206. More specifically, the data entries are evaluated in relation to a set of membership rules 222, where the set includes rules for associating data entries with the given structured collection procedure. Data entries are in turn input by the membership module into the patient log for the patient with or without an association to the given structured collection procedure. Membership rules 606 are also stored in a data store residing on the computing device.

Three fundamental issues unique to manual-entry systems and structured testing are: (1) the user can set or change the date and time of logged events; (2) entries can be independent of blood glucose values; and (3) existing entries can be deleted. These issues create substantial problems for structured test management. The central idea behind structured testing is that measuring blood glucose in a structured (as opposed to ad-hoc) way can give patients and health-care providers key insights into improving the patient's diabetes management. To complete a structured test, the user must therefore measure their blood glucose at specific times relative to certain events. It is because timing of blood glucose measurements is so important that the extra flexibility of the manual-entry system causes problems. In a blood glucose meter, it is relatively clear whether a given measurement meets the criteria for inclusion in a structured test because the meter actually records the blood glucose value and its corresponding time (from the device's clock). In a manual-entry device, however, the situation is much more fluid and difficult to manage.

Problems associated with manual-entry devices are best illustrated by an example. Suppose the user is executing a Testing in Pairs (TiP) structured test associated with exercise event. The TiP test specifies that the trigger in the exercise event and that the post-exercise blood glucose measure must occur in a 60 minute window after the event. But consider the following reasonable scenario:

1. The structured test began on Sunday;
2. On Monday morning, the user measured their blood glucose at 6:30 AM. They took a half-hour walk from 7 to 7:30, and measured their blood glucose again at 10 AM. They recorded none of this in diabetes management application.
3. On Tuesday evening, the user remembers that they didn't log their Monday exercise and related blood glucose measures. They open the diabetes management application and scroll their meter's memory to record the blood glucose at 6:30, record the exercise at 7:00 and use their meter to get the blood glucose at 10. But, since it is now Tuesday, they neglect to reset the date on these events. As far as the diabetes management application is concerned, the events occurred on Tuesday morning, not Monday morning.
4. On Wednesday, when the user logs some something else, they realize the mistake and reset the dates on the three earlier events (from Tuesday to Monday).

Now consider the following five questions:

1. When the user enters the first blood glucose value, should the diabetes management application consider it part of the structured test? Should it allow the user to identify it as such? This is not at all obvious because no exercise has been entered.
2. On Wednesday, the user resets the time of the exercise by a day. At that moment the post-exercise blood glucose is outside the acceptance window for the post event. What happens?
3. What happens if the user makes a blood glucose entry between 6:30 and 10 and tries to include it in the structured test?
4. What happens if the user, when they move the post-exercise blood glucose reading, mistakenly changes the time to 10 PM (outside the allowable range)?
5. What happens if the user, after moving the 6:30 AM event but before moving the 10 AM event, creates a new pre-exercise event at 7 AM on Tuesday?

This disclosure presents an analysis of the problem of structured test membership in a manual-entry situation and solutions in light of this analysis.

Before considering possible solutions, a way is needed to describe the problems and issues that could arise with respect to structured testing in a manual-entry system. Such a description is necessary to have confidence that a proposed solution will actually work and not leave open issues. The previous section identified three aspects unique to manual-entry systems: editable date/time, non-blood glucose entries, and the ability to delete existing entries. As a first step toward simplifying the problem, data entries are assumed to be blood glucose measures. While other types of data entries are ignored for the analysis set forth below, it is readily understood that the analysis (including membership rules) could be extended to other types of non-blood glucose entries. As a second step towards simplifying the analysis, it is noted that editing an existing logbook record is conceptually equivalent to deleting the original record and creating a new record with the changed values. Therefore, this analysis need only consider creating new records and deleting existing records. Finally, the analysis is applied to Testing in Pairs (TiP) testing and Three-day Profile (3DP) testing separately because they are very different in terms of their requirements and constraints. Again, it is envisioned that this type of analysis can be extended to other types of structured tests.

With respect to a Testing in Pairs regimen, there is only a need to address a regimen that is in progress; completed regimens are assumed to be "locked" and cannot be changed. For an in-progress TiP test, each relevant data entry (where relevant means "contains a blood glucose value and occurs after the TiP regimen started") must fall into one of three states:

1. The entry in question is not part of the structured test which is referred to herein as the "OUT" state.
2. The entry in question is potentially half of a pair whose other half is not yet available which is referred to herein as the "SINGLE" state.
3. The entry in question is part of a completed pair which is referred to herein as the PAIRED state.

Possible situations that any solution must address are enumerated as follows:

Deleting an OUT entry
Deleting a SINGLE entry
Deleting a PAIRED entry
Creating a relevant new entry in the presence of existing entries, The last of these requires further expansion: what are the meaningful possible combinations of structured tests in the "presence" of a new entry? The time limits on TiP pairs give us a way to answer this. Each TiP test has an acceptance time "window" in which a TiP pair can occur. For example, the time window for a TiP test pertaining to an exercise event is 6 hours. Let w be the maximum time window for the type of TiP in progress. Then, for a new logbook entry at time t, we need only concern ourselves with existing logbook entries in the time interval [t-w, t+w]. With respect to this interval, note that "OUT" entries are not relevant—they do not affect the state of the new entry. Therefore, potential solutions need only deal with the following situations:

There are no PAIRED or SINGLE entries in the window
There are no PAIRED entries in the window, and one SINGLE entry
There are no PAIRED entries in the window, and more than one SINGLE entry
There is a PAIRED entry in the window, but no SINGLE entry
There is one PAIRED entry and one SINGLE entry in the window
There is one PAIRED entry and more than one SINGLE entry in the window
There are multiple PAIRED entries and no SINGLE entry in the window There are multiple PAIRED entries and one SINGLE entry in the window There are multiple PAIRED and multiple SINGLE entries in the window, Note that in the above, it is sufficient for one member of a pair to fall in the window to count as a single PAIRED entry in the window. Added to the three earlier scenarios (for delete), twelve possible scenarios have been identified that can occur in a manual-entry system with respect to a running TiP regimen. Potential solutions must address every one of these situations, either by providing explicit rules for dealing with it, or explicit rules for precluding it.

The question at hand is how to manage membership of logbook entries in a structured test. It is not really an option to have the user manage membership with no enforcement of restrictions; that would defeat the purpose of structured testing. There are two possible general approaches. First, allow the user to manage membership of logbook entries in a structured test, with guidance and restriction by the system. This approach is referred to as the explicit management approach. Second, automatically determine membership based on defined criteria. This approach is referred to as the implicit management approach. Under either approach, constraints and rules must be identified that insure that all of the situations identified in the problem analysis set forth above are met.

Starting with the explicit management approach, membership rules 606 are further developed for a TiP test. The primary issue in the explicit approach is providing simple and clear restrictions so that the user is not confused when the system has to reject an attempt to associate a data entry with the structured test. Three global constraints are sufficient to insure that the explicit approach works correctly for TiP test. The three global constraints are as follows:

CE1: Only one SINGLE allowed at a time,
CE2: Pairs cannot overlap or be nested.
CE3: Pairs must be started in chronological order, Guided by these three global constraints, particular membership rules 606 can be enumerated for each of the twelve possible scenarios. These membership rules collectively define the membership rule set which pertains to a TiPs test under the explicit approach and are set forth in the table below.

| Situation | Explicit Approach Logic |
|---|---|
| S1: Deleting an OUT entry | Allow |
| S2: Deleting a SINGLE entry | Allow |
| S3: Deleting a PAIRED entry | Per CE1, if there are existing SINGLEs, do not allow. Otherwise, allow and set the remaining entry to SINGLE. |
| S4: Create, no PAIRED or SINGLE entries in the window | Allow |
| S5: Create, there is one SINGLE entry in the window | Per CE1, if the new entry and the existing SINGLE make a pair, allow and set both to PAIRED. Otherwise, do not allow per CE1 |
| S6: Create, there are no PAIRED and multiple SINGLE entries in the window | Precluded by CE1 |
| S7: Create, there is a PAIRED entry in the window but no SINGLE entry | Per CE1, if there are existing SINGLEs anywhere, do not allow. Per CE2, if the new entry is between the existing PAIR, do not allow. Otherwise, set the new entry to SINGLE |
| S8: Create, there is a PAIRED entry and a SINGLE entry in the window | Per CE1, if the existing SINGLE and the new entry do not make a pair, do not allow. Per CE2, if the new entry falls within the existing pair, do not allow. Otherwise, pair the new entry and the existing SINGLE and set both to PAIRED |
| S9: Create, there is a PAIRED entry and multiple SINGLE entries in the window | Precluded by CE1 |
| S10: Create, multiple PAIRED entries and no SINGLE entry in the window | Per CE2, if the new entry falls within one of the existing pairs, do not allow. Per CE3, if the new entry falls before either of the existing pairs, do not allow. Per CE1, if there are existing SINGLEs anywhere, do not allow. Otherwise, allow and set the new entry to SINGLE |
| S11: Create, multiple PAIRED entries and one SINGLE entry in the window | Per CE2, if the new entry falls within one of the existing pairs, do not allow. Per CE3, if the new entry falls before either of the existing pairs, do not allow. Per CE1, if the new entry and existing single do not make a pair, do not allow. Otherwise, pair the new entry and the existing single, setting both to PAIRED |
| S12: Create, multiple PAIRED entries and multiple SINGLE entries in the window | Precluded by CE1 |

Manual data entries can be evaluated in relation this membership rule set by the membership module 602 in the manner further described below.

The primary issue in the implicit approach is somewhat different from the explicit approach. In the implicit management approach, it is important to leave options open and await further actions by the user. Therefore, in the implicit approach we employ the following constraints:

CI1: Pairs cannot overlap or be nested.

From this constraint, particular membership rules for the implicit approach can be enumerated for each of the twelve possible scenarios. These membership rules collectively define the membership rule set which pertains to a TiPs test under the implicit approach and are set forth in the table below.

| Situation | Implicit Approach Logic |
| --- | --- |
| S1: Deleting an OUT entry | Allow |
| S2: Deleting a SINGLE entry | Allow |
| S3: Deleting a PAIRED entry | Set the remaining entry to SINGLE and apply the logic for a new entry to it. |
| S4: Create, no paired or single entries in the window | Set the new entry to SINGLE |
| S5: Create, there is one SINGLE entry in the window | If the new entry and the existing SINGLE make a pair, set both to PAIRED. Otherwise, make the new entry SINGLE. |
| S6: Create, there are no PAIRED and multiple SINGLE entries in the window | If the new entry can be paired with one of the existing singles, pair it with the SINGLE that encompasses the largest window less than w and set any SINGLE entries that fall within this window to OUT per CI1. Otherwise, set the new entry to SINGLE. |
| S7: Create, there is a PAIRED entry in the window but no SINGLE entry | Per CI1, if the new entry is between the existing PAIR, make the new entry OUT. Otherwise, set the new entry to SINGLE |
| S8: Create, there is a PAIRED entry and a SINGLE entry in the window | Per CI1, if the new entry falls within the existing pair, make the new entry OUT. If the new entry and the existing SINGLE for a pair, set both to PAIRED Otherwise, set the new entry to SINGLE |
| S9: Create, there is a PAIRED entry and multiple SINGLE entries in the window | Per CI1, if the new entry falls within the existing pair, make the new entry OUT. If the new entry can be paired with one of the existing singles, pair it with the SINGLE that encompasses the largest window less than w and set any SINGLE entries that fall within this window to OUT per CI1. Otherwise, set the new entry to SINGLE |
| S10: Create, multiple PAIRED entries and no SINGLE entries in the window | Per CI1, if the new entry falls within one of the existing pairs, set the new entry to OUT. Otherwise, set the new entry to SINGLE |
| S11: Create, multiple PAIRED entries and one SINGLE entry in the window | Per CI1, if the new entry falls within one of the existing pairs, set the new entry to OUT. If the new entry matches the existing SINGLE but the resulting pair intersects an existing pair, set the new entry to OUT. If the new entry matches the existing SINGLE and the resulting pair does not intersect an existing pair, set the new entry and the existing SINGLE to PAIRED. Otherwise, set the new entry to SINGLE |
| S12: Create, multiple PAIRED entries and multiple SINGLE entries in the window | Per CI1, if the new entry falls within one of the existing pairs, set the new entry to OUT. If the new entry matches an existing SINGLE but the resulting pair intersects an existing pair for all such SINGLEs, set the new entry to OUT. If the new entry matches an existing SINGLE and the resulting pair does not intersect an existing pair, choose the SINGLE that encompasses the largest window less than w and set any SINGLE entries that fall within this window to OUT per CI1. Set the new entry and the matching SINGLE to PAIRED. Otherwise, set the new entry to SINGLE |

Manual data entries can be evaluated in relation to this membership rule set by the membership module 602 in the manner further described below.

Turning to the Three-day profile (3DP) regimen, there is only a need to address a structured test that is in progress as was the case with TiP regimen. Thus, completed tests are assumed to be "locked" and cannot be changed. In one regard, 3DP tests are simpler than TiP tests because there are predefined time slots and each time slot has specific requirements. In another regard, 3DP tests are more complex than TiP tests because there is no simplifying concept like "pair" which can reduce the problem analysis space (the concept of "day" in 3DP at first looks like it might be useful, but because a 3DP day has no real relationship to a calendar day, that proves to not be true). Nonetheless, a 3DP regimen can be analyzed in terms of "windows" similar to those used for TiPs tests. Each of the 7 "slots" in a 3DP day has time constraints based on "normal" meal and bed times that the user selects. For example, the user may have indicated that breakfast normally occurs at 7 am. To map a data entry for an event to a slot, the event should fall within a defined time-window associated with the slot (e.g., within 30 minutes of the designated meal time). Additionally, the event should meet the other criteria for the slot. For example, the data entry may specify an indicator for the slot (e.g., pre-breakfast, post-breakfast, pre-lunch, etc.). To map the data entry to a slot, the indicator should also match the indicator associated with the slot. Other types of criteria are also contemplated by this disclosure. When each of the criteria for the slot is met, the data entry is mapped to the slot and thus associated with the structured test. Accordingly, each data entry for a 3DP regimen falls into one of two states:

1. The entry in question is not part of the structured test; referred to herein as the OUT state.
2. The entry in question is filling a slot in the structured test; referred to herein as the SLOTTED state.

The various create and delete scenarios are now enumerated based on the possible states. Delete is straightforward: deleting either an OUT entry or a SLOTTED entry. With respect to a new relevant entry, the following situations are possible:

The entry does not match any slot

The entry matches a slot that has a SLOTTED entry

The entry matches a slot for which there is no SLOTTED entry.

Thus, for 3DP there are only five possible scenarios a solution must address or preclude.

Membership rules for the three-day profile test are considerably simpler because of its division into days and "slots" (corresponding to meal times and bedtimes). Only two global constraints are sufficient for both the implicit and explicit approaches.

C3DP1: Only one entry per slot

C3DP2: Every entry must match a slot

Guided by these global constraints, particular membership rules can be enumerated for each of the possible scenarios.

These membership rules collectively define the membership rule set which pertains to a 3DP test and are set forth in the table below.

| Situation | Explicit Approach | Implicit Approach |
|---|---|---|
| Delete an OUT entry | Allow | Allow |
| Delete a SLOTTED entry | Allow | Allow |
| New entry does not match any slot | Do not allow per C3DP2 | Make new entry OUT |
| New entry matches a slot for which there is a SLOTTED entry | Do not allow per C3DP1 | Make new entry OUT |
| New entry matches a slot for which there is no SLOTTED entry | Put entry in the slot, make it SLOTTED | Put entry in the slot, make it SLOTTED |

Manual data entries can be evaluated in relation to these membership rules 606 by the membership module 602 in the manner further described below.

Figure 7:
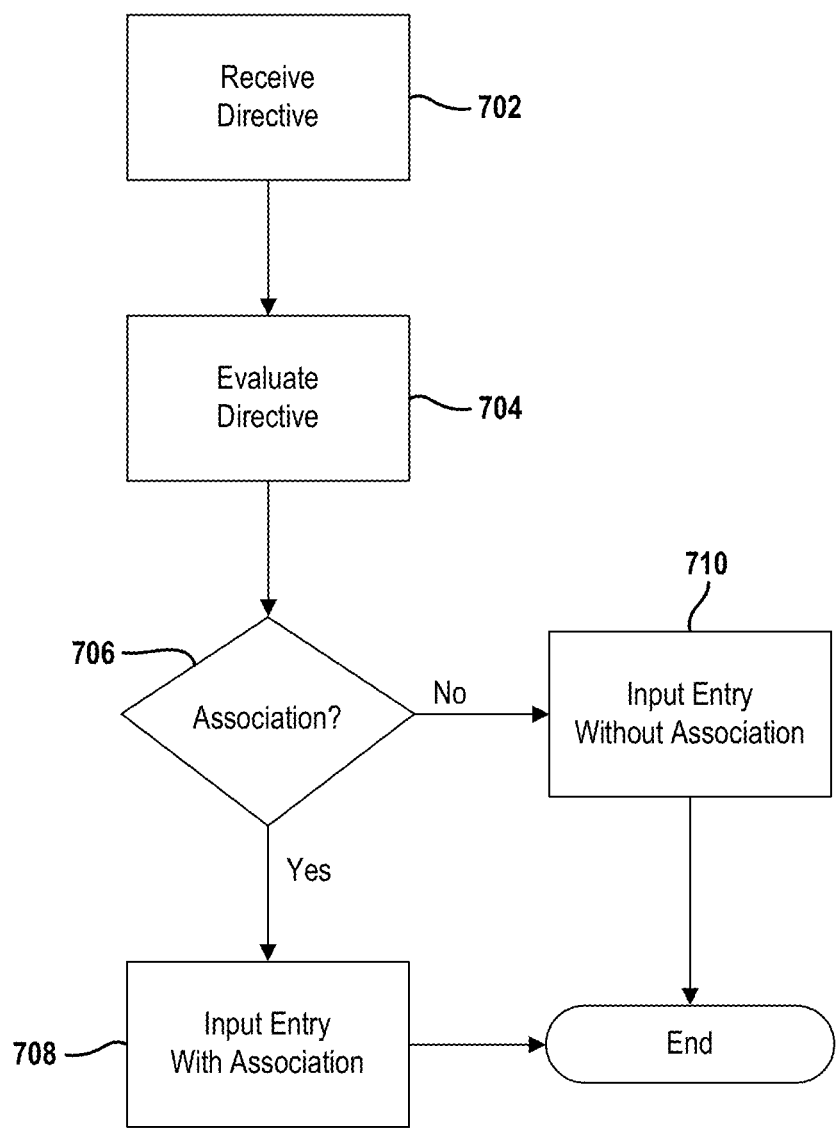
FIG. 7 is a flowchart depicting an exemplary method for managing manual entries of blood glucose measures in relation to a structured test managed by a portable computing device.

FIG. 7 provides an overview of this exemplary method 700 for managing manual data entries of blood glucose measures in the context of a diabetes management application 200 residing on a portable computing device. In an exemplary embodiment, various data related to the patient's diabetes care may be logged by the patient via the diabetes management application 200 into a logbook residing on the portable computing device. For example, during the structured test, the patient may be prompted to manually input data entries for blood glucose measures taken in accordance with the structured test. Such data entries may include blood glucose measures as well as a date and time at which the blood glucose measure was taken by the patient. Of note, this data is provided manually by the patient as opposed to being generated or otherwise provided automatically by the diabetes management application 200. The patient may also input data entries which are unrelated to the ongoing structured test. For example, the patient may input a data entry pertaining to a meal, exercise or some other type of health data. In this case, the data entries are not in response to or associated with the ongoing structure test but nonetheless captured by the diabetes management application 200.

In operation, the diabetes management application 200 is configured to receive directives pertaining to data entries in the logbook as indicated at 702. Directives may include but are not limited to creating, deleting or updating data entries in the logbook. Thus, each directive pertains to one or more particular data entries whether it be deleting an existing data entry or creating a new data entry. Directives are evaluated at 704 using membership rules to determine whether the directive is permissible or not as it relates to the ongoing structured test. In the case of creating a new data entry in the logbook, the data entry may be created with an association to the structured test as indicated at 708 or without an association to the structured test as indicated at 710.

Figure 8:
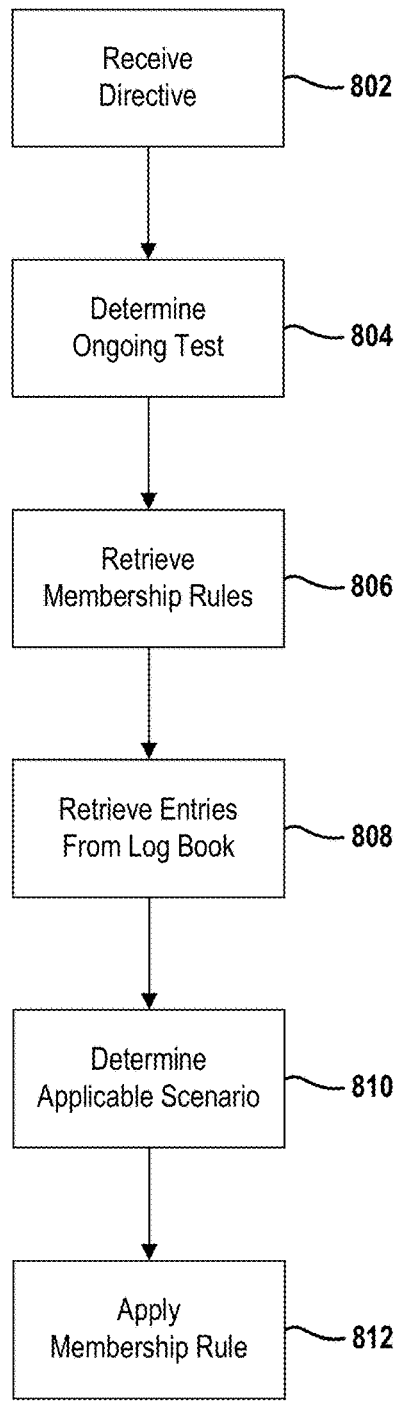
FIG. 8 is a flowchart depicting an exemplary method for evaluating data entries implemented by a membership module of the diabetes management application.

FIG. 8 further depicts the evaluation process as implemented by the membership module 602 of the diabetes management application 200. Upon receiving a directive at 802 from the user, the membership module 602 first determines the type of structured test that is being managed for the patient. In an exemplary embodiment, each structured test may have a unique type identifier (e.g., type 1=TiP, type 2=3DP, etc.). The type identifier for the ongoing structured test may be stored in a data store 604 accessible to the membership module 602, where the data store 604 contains data for the ongoing structure test and is maintained by the test module 206. In this way, the membership module 602 may determine the type of structured test by retrieving the type identifier from the data store 604.

Membership rules vary depending on the management approach and the type of structured test. In an exemplary embodiment, the management approach (i.e., implicit or explicit) may be a preconfigured parameter of the device or a user configurable parameter accessible to the membership module 602. Accordingly, a set of membership rules should be provided for each unique combination of management approach and test type that is supported by the diabetes management application 200. Given the management approach setting and the retrieved test type, the membership module 602 can retrieve at 806 an applicable set of membership rules 606 for evaluating the user directive.

Next, the membership module 602 retrieves at 808 any previous data entries stored in the logbook and associated with the ongoing structured test. In an exemplary embodiment, each structured test administered by the test module 206 is assigned a unique test identifier. The unique test identifier for the ongoing structured test is in turn maintained in the data store 604 by the test module 206. When logging data entries into the logbook, the membership module 602 can access the test identifier for the ongoing structure test and, if applicable, tag the data entries being entered into the logbook with the unique identifier for the ongoing structure test. To retrieve data entries for the ongoing structure test, the membership module 220 can likewise retrieve the test identifier from the data store 604 and, using the retrieved test identifier, retrieve any previous data entries associated with the ongoing structure test from the logbook 203.

From the user directive and the retrieved data entries, the membership module 602 can then determine at 810 the applicable scenario from a set of possible scenarios. For example, assume a directive to create a new data entry in the context of an ongoing TiP test. Should the membership module 602 retrieve one SINGLE data entry in the time window for the ongoing TiP test, the membership module 602 would deem the situation S5 (see scenario table above) and in turn retrieve the corresponding membership rule which applies to this scenario.

Lastly, the membership module 602 applies the corresponding membership rule as indicated at 812. Continuing with the example above, if the new entry and the existing entry meet the pairing criteria for forming a pair, the membership module 602, operating in accordance with the explicit approach, would permit the new entry to be paired with the existing entry and thus associated with the ongoing TiPs test. If the new entry and the existing entry failed to meet the pairing criteria, the membership module 602, operating in accordance with the explicit approach, would tell the user the that the entry cannot be part of the structured test, and ask the user to either modify the entry or remove it from the structured test. In contrast, the membership module 602, operating in accordance with the implicit approach, would permit the new entry to be paired with the existing entry if the new entry and the existing entry meet the pairing criteria for forming a pair. On the other hand, if the new entry and the existing entry failed to meet the pairing criteria, the membership module 602, operating in accordance with the implicit approach, would not associate the new data entry with the ongoing TiP test and permit entry into the logbook. It is to be understood that the pairing criteria are defined by the structured test and thus operate independent from the membership rules set forth in this disclosure. It is to be further understood that only the relevant steps of the membership module 602 are discussed above in relation to FIG. 8, but that other software-implemented instructions may be needed to control and manage the overall operation of the system.

Below the five questions presented above are re-presented with comments describing how the explicit and implicit approaches with the proposed constraints would behave:
1. When the user enters the first blood glucose value, should the diabetes management application consider it part of the structured test? Should it allow the user to identify it as such? This is not at all obvious because no exercise has been entered.

This issue is resolved by the overall assumption that only blood glucose entries are considered. Therefore, in the implicit approach the blood glucose value is SINGLE and in the explicit approach the user has the option (which we presume they select) to include the result in the structured test.

2. On Wednesday, the user resets the time of the exercise by a day. At that moment the post-exercise blood glucose is outside the acceptance window for the post event. What happens?

Presume the user first resets the date on the "before" event (the sequence is the same if the move the "after" event first). In both implicit and explicit approaches, both the "before" the "after" events go to the SINGLE state. Then, when the "before" event is moved, both events return to PAIRED state.

3. What happens if the user makes a blood glucose entry between 6:30 and 10 and tries to include it in the structured test?

This is prohibited in both the implicit and explicit approaches. In the implicit approach, the new event would be OUT. In the explicit approach, the user would be told they cannot include the result in the structured test.

4. What happens if the user, when they move the post-exercise blood glucose reading, mistakenly changes the time to 10 PM (outside the allowable range)?

In the implicit approach, the new event would be marked SINGLE. In the explicit approach, the user would be told there is an error because there is already a SINGLE event.

5. What happens if the user, after moving the 6:30 AM event but before moving the 10 AM event, creates a new pre-exercise event at 7 AM on Tuesday?

In both approaches, the new event will form a pair with the remaining Tuesday post-exercise. When the user attempts to move that post event, the implicit approach will allow it and set the new event to SINGLE. In the explicit approach, the user will not be allowed to move the post event until providing a pair for the Monday pre event.

In the context of a structured test, blood glucose measures are typically associated with a user event, such as a meal, exercise, bedtime, etc. For each user event, the structured test can specify an expected time for the event. Although a default value may be provided, the expected time for a given event is preferably a value configured by the user. For example, the user may define the expected time for breakfast as 7:00 AM and/or the expected time for bedtime as 10:30 PM.

The structured test can also specify one or more collection actions for obtaining blood glucose measures from a patient as noted above. In many instances, the collection action is associated with a user event. An acceptance window for the collection action may be defined such that the acceptance window is calculated from the expected time for the event and specifies a range of times for accepting the blood glucose measure. For example, the acceptance interval for a pre-meal blood glucose measure may be defined as two hours before or after the expected meal time; whereas, the acceptance interval for a post-meal blood glucose measure is defined as one to four hours after the meal time if logged or otherwise relative to the schedule meal time. It is readily understood that the specified range of acceptance windows will vary depending on the event type. Furthermore, it is understood that the specified ranges may be defined in accordance with medical guidelines and standards. Since manual entries may be input at anytime, it is noted that the acceptance window pertains to the time at which the measure was taken and not the time input by the user.

Continuing with the examples of the TiP test and the three-day profile test, the table below sets forth the allowed ranges and default values for the parameters associated with these two exemplary structured tests.

| Event | Parameter | Description | Allowed Range | Default Value | Used In |
|---|---|---|---|---|---|
| Test start | Start date | The date on which a 3DP will start | Today (if current is before the scheduled breakfast time) or Tomorrow to 7 months from now | Tomorrow | 3DP |
| Breakfast | Normal breakfast time | Used as the basis for determining pre-meal acceptance window, post-meal acceptance window if there is no pre event, and pre-meal reminder times | Any time value | 7:00 AM | Meal-based TiP, 3DP |
| Lunch | Normal lunch time | Used as the basis for determining pre-meal acceptance window, post-meal acceptance window if there is no pre event, and pre-meal reminder times | Any time value | 12:00 PM | Meal-based TiP, 3DP |

-continued

| Event | Parameter | Description | Allowed Range | Default Value | Used In |
|---|---|---|---|---|---|
| Dinner | Normal dinner time | Used as the basis for determining pre-meal acceptance window, post-meal acceptance window if there is no pre event, and pre-meal reminder times | Any time value | 7:00 PM | Meal-based TiP, 3DP |
| Any Meal | Post-meal reminder interval | When the reminder for a bG test after the meal should occur, measured from the pre-meal event time (if no pre-event occurs, no post reminder occurs) | N/A; value not user editable | 2 hours after | Meal-based TiP, 3DP |
| | Pre-meal reminder interval | When the reminder for a bG test before the meal should occur, measured from the scheduled meal time | N/A; value not user editable | 15 min before | Meal-based TiP, 3DP |
| | Pre-meal test acceptance time window | The interval, relative to the scheduled meal time, in which a pre-meal event is acceptable | −2 h to +2 h | N/A | Meal-based TiP, 3DP |
| | Post-meal test acceptance time window | The interval, relative to the logged pre-meal event (if present, otherwise relative to scheduled meal time), in which a post-meal event is acceptable | 1-4 h | N/A | Meal-based TiP, 3DP |
| Bedtime | Normal bedtime | Used as a basis for determining pre-event acceptance windows and reminder times | Any time value | 11:00 PM | Bedtime-based TiP, 3DP |
| | Event reminder | When, relative to scheduled bed time, the user should receive a reminder to log pre-bedtime bG | N/A | 15 min before | Bedtime-based TiP, 3DP |
| | Event acceptance window | When, relative to scheduled bed time, the bedtime bG can be logged | −2 h to +2 h | N/A | Bedtime-based TiP, 3DP |
| Fasting | Event acceptance window | When, relative to logged bedtime, a fasting bG can be logged | 2 h to 18 h | N/A | Bedtime-based TiP |
| Exercise | Pre-event reminder | When a reminder to log pre-exercise bG should occur | Any time value | Current time | Exercise TiP |
| | Post-event reminder | When a reminder to log post-exercise bG should occur after logged pre-exercise event | 15 min to 5 hours | 1 hour | Exercise TiP |
| | Post-event acceptance window | The time window, relative the pre-exercise bG, in which a post-exercise bG is acceptable | 15 min to 6 hours | N/A | Exercise TiP |
| High bG | Hyperglycemic limit value | The minimum bG value that qualifies as a High bG value for the TiP | Legal bG range as defined in Table 3 | 140 mg/dL | High bG TiP |
| | Post-event reminder | When a reminder to take a post-High bG reading should occur, relative to the logged high bG reading | 15 min to 3 hours | 1 hour | High bG TiP |
| | Post-event acceptance window | The time window, relative to the logged high bG reading, in which a post-High bG is acceptable | 15 min to 4 hours | N/A | High bG TiP |
| Low bG | Low bG threshold | The maximum bG value that qualifies as a Low bG value for the TiP | Legal bG range as defined in Table 3 | 70 mg/dL | Low bG TiP |
| | Post-event reminder | When a reminder to take a post-Low bG reading should occur, relative to the logged low bG reading | 15 min to 30 min | 15 min | Low bG TiP |

| Event | Parameter | Description | Allowed Range | Default Value | Used In |
|---|---|---|---|---|---|
| | Post-event acceptance window | The time window, relative to the logged low bG, in which a post-Low bG is acceptable | 15 min to 1 hour | N/A | Low bG TiP |
| Insulin | Pre-event reminder time | The time when a reminder to take/log insulin should occur | Any time value | Current time | Insulin TiP |
| | Post-event reminder interval | The interval, relative to the pre-event time, when a reminder should occur to take the post-insulin bG reading | 1 h to 22 h | 12 h | Insulin |
| | Post-event acceptance window | The time window, relative to the pre-event, in which a post-insulin bG is acceptable | 30 min to 23 h | N/A | Insulin TiP |

In an exemplary embodiment, the system discards pre events that are not completed after 24 hours. To prevent collision with this requirement, the interval for insulin acceptance has been reduced to fall below the overall limit for pairs in TiP test. It is understood that the table presents an exemplary implementation but that other types of parameters and values for these parameters fall within the scope of this disclosure.

In one aspect of this disclosure, the reminder module 208 is configured to manage reminders within the framework set forth above. More specifically, constraints have been designed to ensure that reminders for blood glucose measures occur within the corresponding acceptance window for the blood glucose measures. Two exemplary types of reminders are pre-event reminders and post-event reminders. It is readily understood that constraints for these reminder types can be extended to other types of reminders.

Figure 9A:
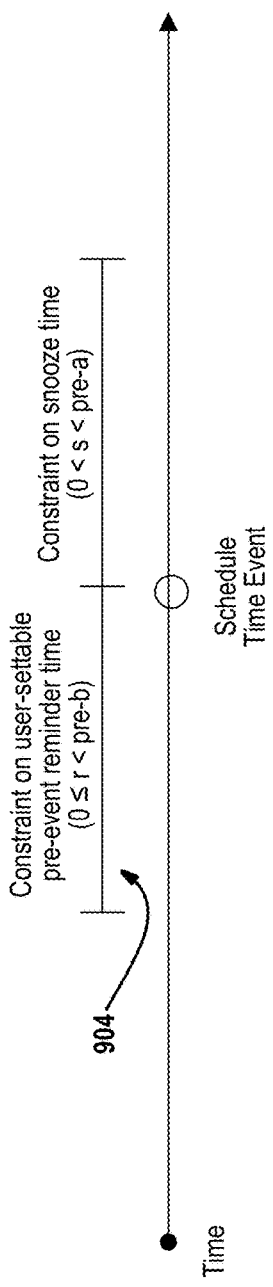
FIGS. 9A and 9B are diagrams illustrating constraints for pre-event and post-event reminders, respectively.

Constraints for reminders associated with pre-event blood glucose measures are further described in relation to FIG. 9A. In this example, an acceptance window 901 for blood glucose measures has been defined before and after the scheduled time of the user event (e.g., a meal time). At this point, an occurrence of the user event is unknown to the system. In one embodiment, a default value for the reminder is a fixed time (e.g., 15 minutes) before the scheduled time of the user event as indicated at 904. To the extent that the reminder may be user defined, the reminder for the pre-event blood glucose measure is constrained to be within the acceptance window but before the scheduled time of the user event. When presented with a reminder, the user may have the option to 'snooze' the reminder for a period of time which may be predefined or user selectable. Subsequent reminders triggered by the snooze feature are also constrained to fall within the acceptance window for the blood glucose measures. In other words, the user is not given the option to snooze a reminder if the reminder would occur outside the acceptance window.

Figure 9B:
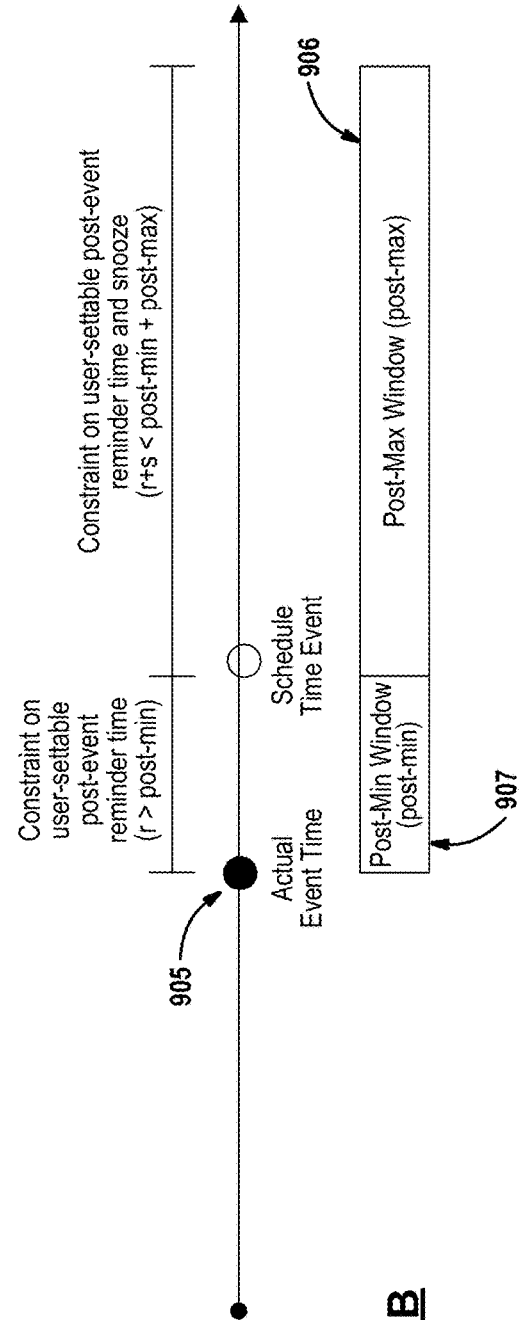

Constraints for reminders associated with post-event blood glucose measures are described in relation to FIG. 9B. This scenario is more complex in that the occurrence of the user event may have occurred before or after the scheduled time of the user event. In the event that a time for the occurrence of the user event is logged with the system, the acceptance window as well as reminders for post-event blood glucose measures may be set relative to the logged time for the event. For example, the acceptance window may be defined after the occurrence of the event as shown 906. In this example, there is a minimum period of time before the blood glucose measure can be taken, for example, after eating a meal. When the occurrence of the event is unknown, the acceptance window is defined in relation to the scheduled time for the event (not shown). In one embodiment, the default value for the reminder coincides with the beginning of the acceptance window. To the extent that the reminder may be user defined, the reminder for post-event blood glucose measures is constrained to occur within the acceptance window. When presented with a reminder, the user may have the option to 'snooze' the reminder for a period of time which may be predefined or user selectable. In either case, the snooze period is also constrained so that subsequent reminders fall within the acceptance window for the blood glucose measures.

Figure 10:
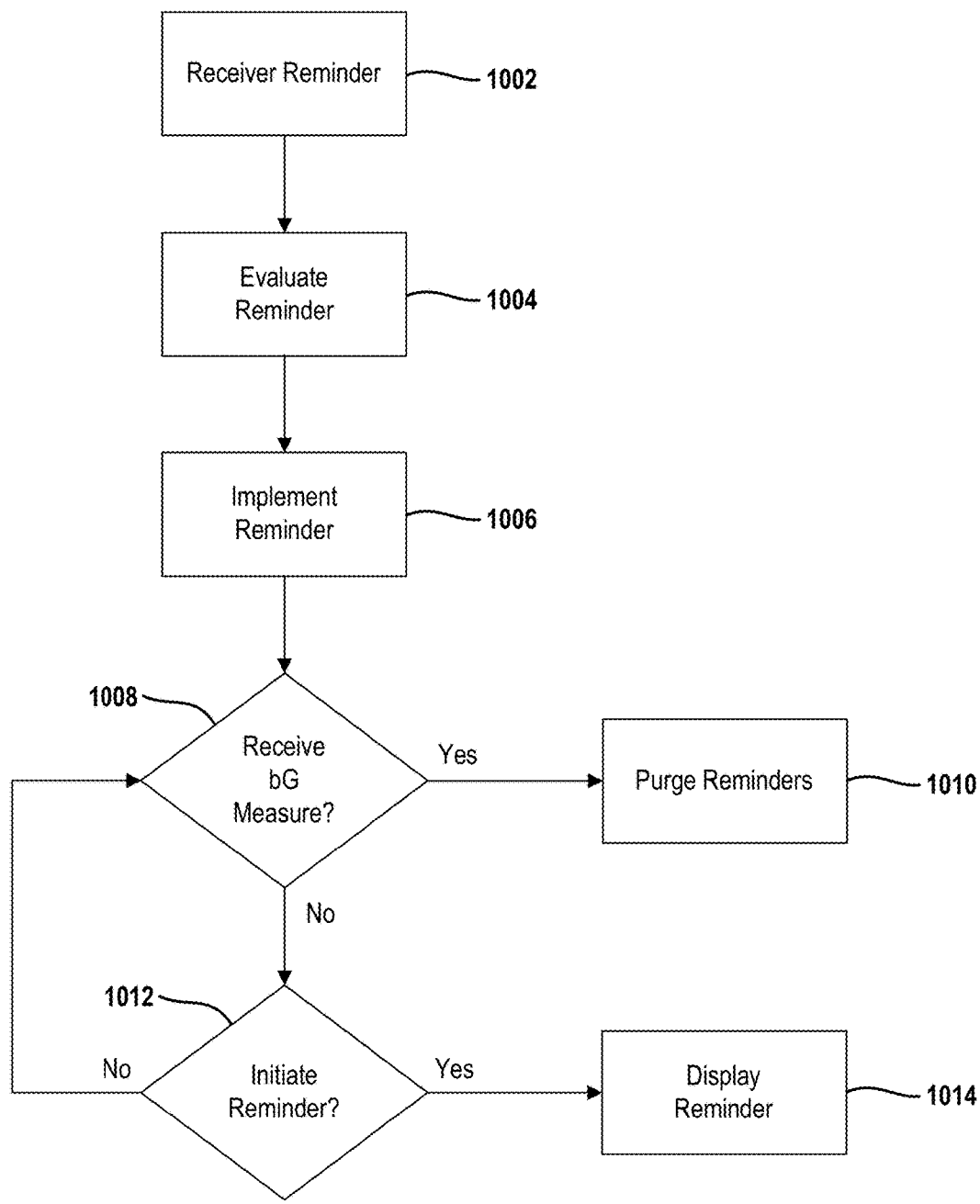
FIG. 10 is a flowchart depicting an exemplary method for managing reminders in a diabetes management application.

FIG. 10 provides an overview of this exemplary method for managing reminders by the reminder module of the diabetes management application 200. The reminder module provides a user interface which enables a user to configure reminders, including selecting attributes of reminders associated with an ongoing structured test. When creating a reminder, the user specifies various attributes associated with the reminder which are captured and received at 1002 by the reminder module. Exemplary attributes may include a name, a reminder type, a date and time to initiate the reminder, notification type, and snooze period. Other types of reminder attributes are contemplated by this disclosure.

Each reminder is in turn evaluated at 1004 by the reminder module. In particular, the attributes for a given reminder are evaluated in relation to a set of constraints. In a simplified example, the date and time to initiate the reminder cannot occur in the past. In a more robust example, the date and time to initiate a reminder associated with a blood glucose measure of a structured test must fall within the acceptance window for the blood glucose measure. The reminder module may prompt a user to correct attributes which do not satisfy a particular constraint. Once a reminder satisfies each of the constraints, the reminder may be implemented at 1006 by the reminder module. In one embodiment, alarms for reminders are implemented internally by the reminder module. In an alternative embodiment, the reminder module may log reminders with a calendar application or a notification service which is in turn triggers alarms at the appropriate time. Calendar applications, such as Microsoft Outlook or Rainlendar, are readily found or available for installment on most computing devices. Likewise, notification services are readily accessible in many operating systems, such as the Android operating system. Once a reminder is logged, the reminder module enters a wait state.

Upon receipt of an alarm, the reminder module first determines at 1008 whether a blood glucose measure corresponding to the reminder has taken place. When a corresponding blood glucose measure has been input to the system, the reminder is deleted or purged at 1010 without issuing a notification to the user. In this way, the user is not bothered with stale or unnecessary reminder notifications. When a blood glucose measure has not yet been input by the user, the reminder module confirms that the reminder should be initiated at 1012. In particular, a reminder notification is displayed on a display of the device at 1014 if the current time coincides with the time at which to initiate the reminder; otherwise, the reminder module continues in a wait state. Other types of notifications, such as audible or haptic, are contemplated by this disclosure.

Figure 11:
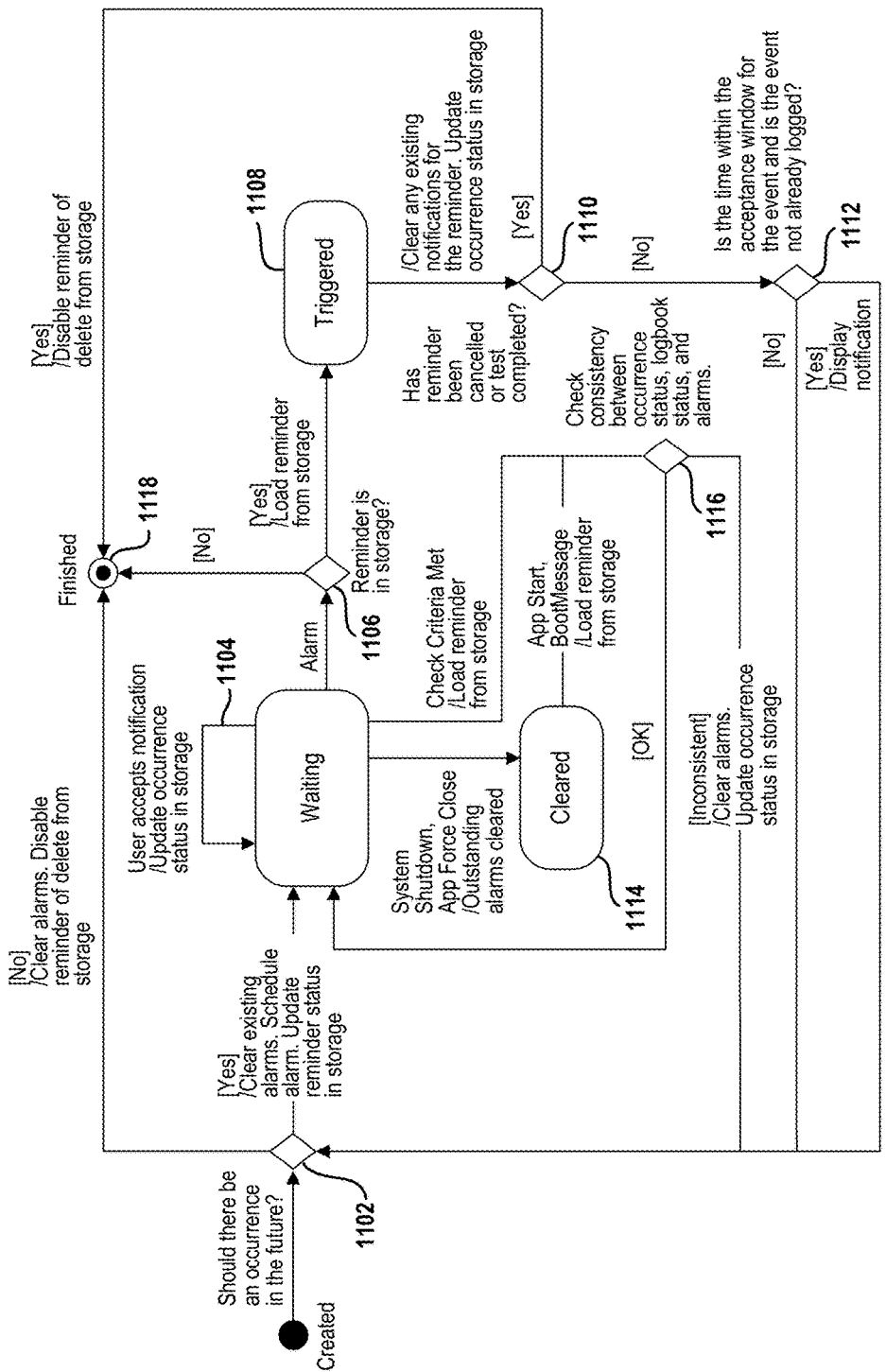
FIG. 11 is a state diagram for handling reminders in a unreliable computing environment by the reminder module.

With reference to FIG. 11, the reminder module 208 has been enhanced to more reliably support reminders in the context of an unreliable computing platform. In one embodiment, the reminder module 208 manages reminders by interfacing with either a calendar application and/or a notification service provided by the operating system as noted above. Since the calendar application and/or notification service may not reliably provide alarms, the reminder module 208 provides additional fail safe functions as further described below.

First, reminders for upcoming events may be logged by the reminder module in a persistent data store 209 associated with the reminder module. Likewise, reminders associated with a structured collection procedure may be logged by the test administration module 206 into the same data store 209. Each reminder specifies a time at which to initiate a reminder. In this way, reminders are maintained by the reminder module 208 for subsequent processing.

In one exemplary embodiment, the reminder module 208 parses each entry in the data store upon the occurrence of a triggering condition at 1116. To determine the occurrence of the triggering condition, the reminder module 208 can be configured to monitor user interactions, for example, with the diabetes management application. In one example, the triggering condition may be each time the user navigates to a particular user interface (e.g., a home screen or data entry screen) of the diabetes management application. Other types of user interactions having a reasonable likelihood of occurrence may also serve as triggering conditions. In other embodiments, the reminder module may operate to parse the data store at regularly scheduled intervals.

For each entry in the data store, the reminder module 208 schedules an alarm or otherwise logs the reminder, for example, with the notification service of the operating system. In one example, the reminder module 208 passes an identifier for the reminder, along with the time at which to initiate a reminder, to the notification service. In another example, the reminder module 208 may log the reminder directly with a calendar application. In either case, a reminder message is sent from the notification service or the calendar application when the current time aligns with the time at which to initiate the reminder.

Upon receipt of a reminder message, the reminder module 208 attempts at 1106 to retrieve a matching reminder from the data store, for example, using an identifier for the reminder embodied in the reminder message. In some instances, the reminder may no longer be found in the data store, for example, if the reminder was input and then subsequently deleted by the user. In these instances, processing of the reminder message is complete as indicated at 1118.

For reminders having a matching entry in the data store, the reminder is validated at 1110 before being displayed to the user. For example, is the time to initiate the reminder in the past? This situation may occur when reminder message is delayed or otherwise not received in a timely manner from the notification service. In another example, the reminder may be associated with a structured test that has been cancelled or completed. In these cases, the reminder is deleted or purged from the data store and processing of the reminder message is complete as indicated at 1110.

The reminder may undergo further validation at 1112. That is, the reminder module 208 determines whether the reminder notification will occur within an acceptance window associated with the reminder. Again, the reminder message from the notification service may be delayed or otherwise not received in timely manner. This step ensures that reminder notifications are presented in a timely manner even in the context of an unreliable computing platform. In addition, the reminder module 208 determines whether the user has already made an entry that matches the acceptance window. This step insures that the reminder notifications are not presented to the user for an action the user has already accomplished.

When the reminder notification falls within the acceptance window and has not already been logged by the user, the reminder notification is presented to the user by the reminder module 208. In an exemplary embodiment, the reminder module 208 may interface with the notification service of the operating system to present the notification as shown, for example, in FIG. 12.

When the user accepts a reminder notification, the reminder module updates the status of reminder progression as shown at 1104. This insures that the reminder persistence remains consistent with what has actually happened, which will help the system resolve the proper system state at 1116 in case of missed alarms.

Lastly, the reminder module 208 will determine at 1102 whether there should be another occurrence of the reminder in the future. In many instances, the user may log a reminder for a single event, such as an upcoming doctor's appointment. This step will not apply to these instances and processing of the reminder message is complete as indicated at 1118. In other instances, the reminder may be part of a group of reoccurring reminders. For example, a three-day profile structured test may prompt the user to obtain blood glucose measures at predefined time slots throughout the course of a given day. Rather than log each of these reminders associated with the structured test, the reminder module 208 can schedule one reminder from the group of reminders with the notification service. When the reminder is part of a group of reoccurring reminders, the reminder module 208 will schedule the next reminder with the notification service and return to a wait state as indicated at 1104; otherwise, processing of the reminder message is completed by deleting the reminder from the data store.

The reminder module 208 is configured to receive at 1114 a system message from the operating system of the device. In one exemplary embodiment, the reminder module 208 registers to receive such messages from the operating system. The system message pertains to an event, such as a system shutdown or an application forced close, which causes outstanding reminders to be cleared from the notification service of the operating system. In response to the system message, the reminder module 208 operates to parse the entries in the data store and applies the same logic at 1116. In this way, cleared reminders are re-scheduled by the reminder module.

Figure 12:
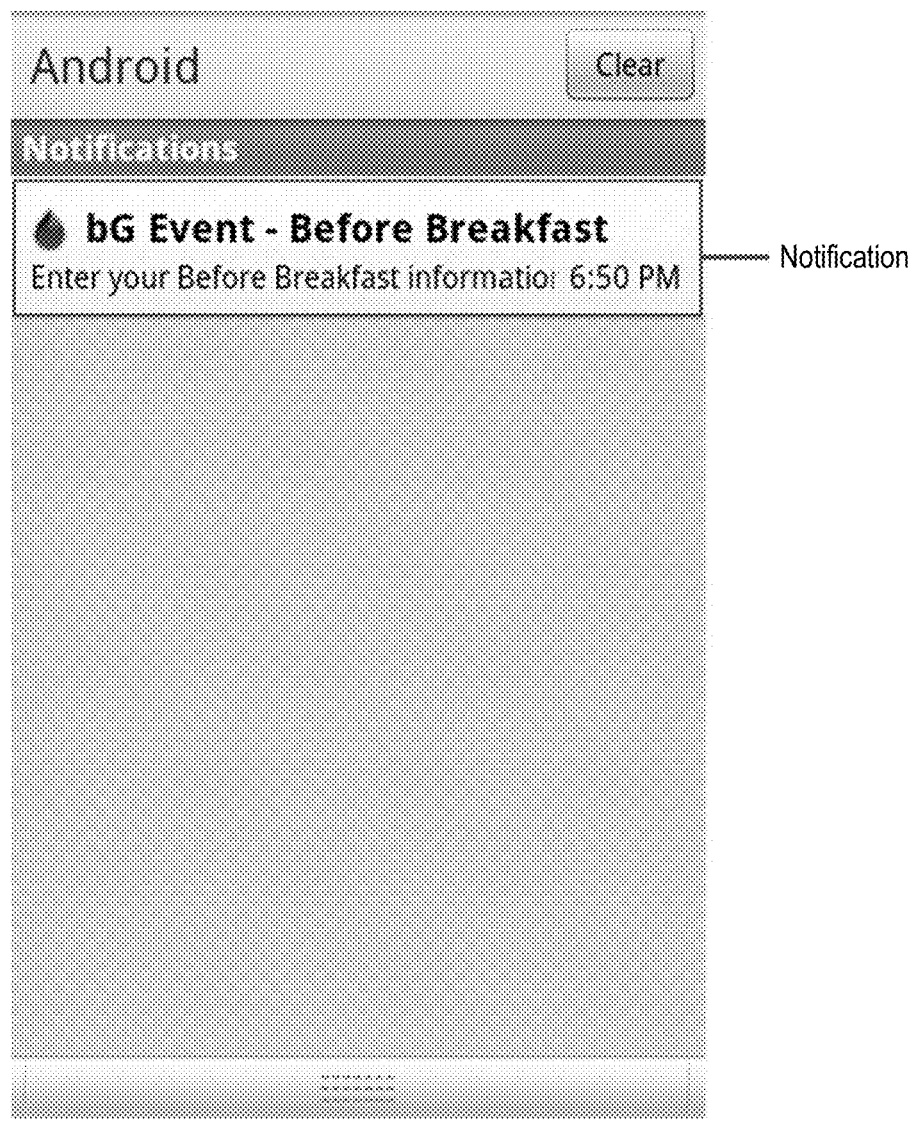
FIG. 12 illustrates an exemplary reminder notification.
Figure 13:
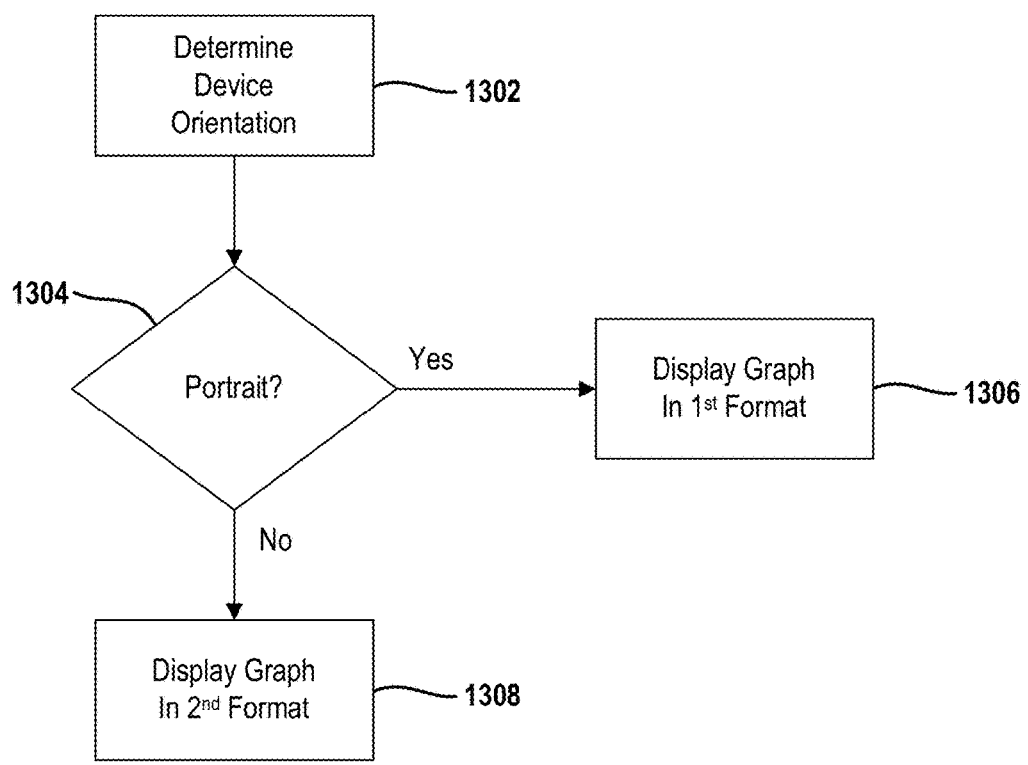
FIG. 13 is a flowchart depicting an exemplary technique for display test results based on orientation of the computing device.

To facilitate manual data entries for blood glucose measures by the user, the data entry interface may be contextualized. In one exemplary embodiment, the data entry interface is contextualized using data input from a reminder notification. During administration of a structured collection procedure, the user may be presented with reminder notifications for a particular collection action associated with the structured collection procedure. For example, the user may be reminded to take a blood glucose measure before eating breakfast as shown in FIG. 12.

In response to the reminder notification, the user may elect to enter a blood glucose measure, clear the notification or take another action in response to the notification, such as to defer the reminder ("snooze"). In an exemplary embodiment, the user may enter a blood glucose measure by selecting the notification. Upon selecting the notification, the user is navigated to an applicable user interface for entering a data entry for a blood glucose measure as shown in FIGS. 3A-3C. The data entry interface includes an input for a blood glucose measure as indicated at 302. Of note, the data entry interface further includes another input at 304 for specifying the type of collection action is associated with the blood glucose measure. Typically, the input for type of collection action is not specified. However, when navigating from a reminder notification, the value of this input 304 is defaulted to the type of collection action associated with the reminder notification. Continuing with the example shown in FIG. 12, the type of collection action would be default to 'Before Breakfast' type, thereby simplifying the entry process for the user.

Another unique aspect of the data entry interface is the use of a status bar indicated at 306 to assist with the input of a blood glucose measure. The status bar represents a range of values for blood glucose measures which may be input. More specifically, the status bar uses a graduated color scheme to represent the values for blood glucose measures, where each color represents a different sub-range of values. For example, red may signify values indicative of a hypoglycemic condition, yellow may signify values that are low but not yet hypoglycemic, green may signify values indicative of a normal condition and blue may signify values indicative of a hyperglycemic condition. Thus, the color signifies the patient's condition. In one embodiment, sub-ranges of values may conform to standard medical guidelines. In other embodiments, sub-ranges of values may calibrated to a particular patient as specified by their physician. While boundaries between sub-ranges may be clearly demarcated, the preferred embodiment blurs the boundaries between the sub-ranges. It is envisioned that the scale may include more or less sub-ranges having the same or different colors.

When creating a new data entry, a blood glucose measure may be input directly into field indicated at 302. Alternatively, a blood glucose measure may be input through the use of a slide-able indicator on the status bar 306. In one embodiment, the position of the indicator correlates to the value of the blood glucose measure displayed in field 302. As the indicator is slid along the status bar, a value of the blood glucose measure displayed in field 302 is changed accordingly. In this way, the user may input a recent blood glucose measure while receiving visual feedback from the status bar as to the condition of their blood sugar level. In addition to the status base, other techniques for input blood glucose measure may include voice recognition, a pinch gesture on a touch display to increase or decrease the value, as well as other gesture based inputs.

In another aspect of this disclosure, results of the 3-day profile test are displayed differently based on the orientation of the computing device. As noted above, the 3-day profile test is administered over the course of three days and specifies seven (7) different time slots for obtaining blood glucose measures on each day. In an exemplary embodiment, results of the 3-day profile test may be displayed in different formats, such as in graph, in a table or statistically. This feature pertains to displaying test results in a graphically format.

When viewing test results graphically, a determination is first made at 1302 as to the orientation of the computing device. More specifically, a determination is made as to the orientation of the display being used to present test results. That is, whether the display (or a longitudinal axis thereof) is oriented vertically or horizontally. One or more accelerometers and/or other types of sensors residing in the computing device may be used to determine the orientation. Such techniques are commonly found in mobile computing devices.

Figure 14A:
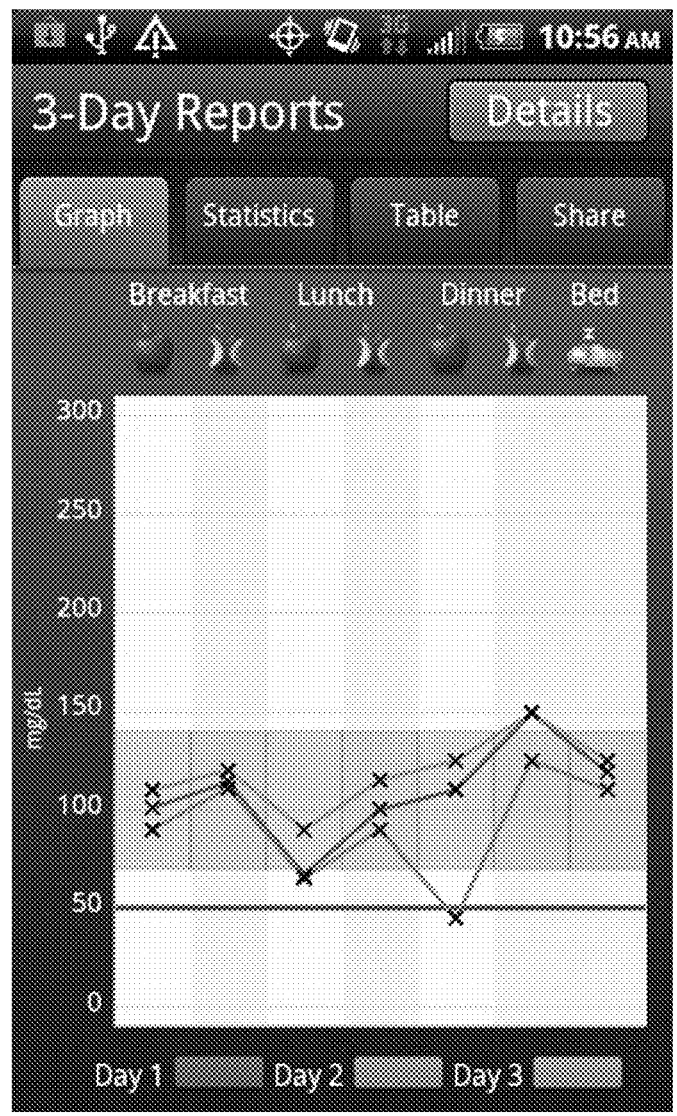
FIGS. 14A and 14B illustrate exemplary formats for reports when the device is orientated vertically and horizontally, respectively.

When the display is orientated vertically, the graph is displayed at 1306 in a format such that blood glucose measures from different days overlay each other as shown in FIG. 14A. In this format, the y-axis represents blood glucose level and the x-axis of the graph represents time during the course of one day. Blood glucose measures from each day of the test are plotted on the graph. Blood glucose measures from a given day are connected by a line which may be color coded to indicate the corresponding day. This format provides for an easier comparison of data across different days.

Figure 14B:
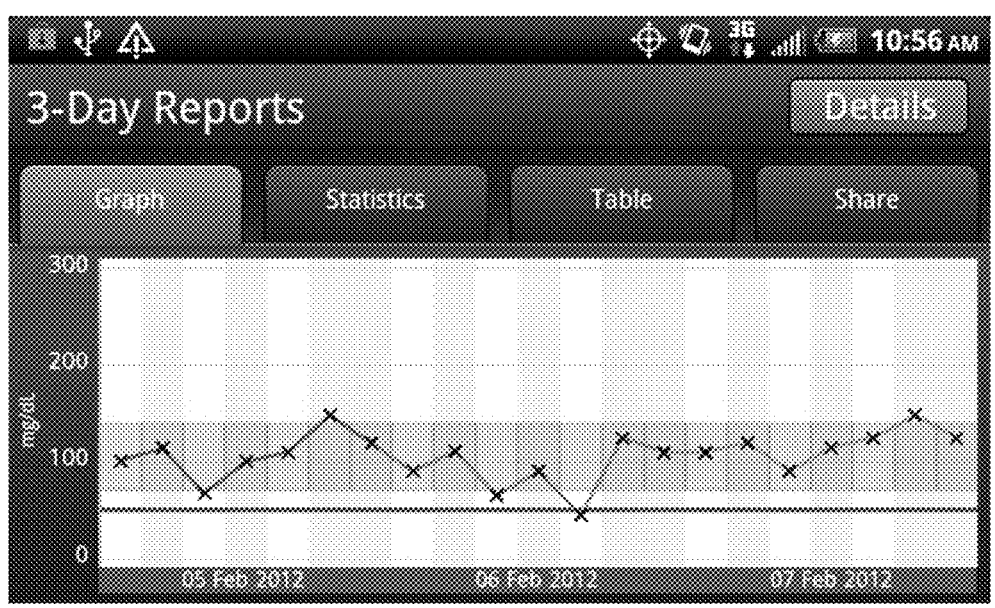

When the display is oriented horizontally, the graph is displayed at 1308 in a second format as shown in FIG. 14B. In this format, the x-axis of the graph represents time over three days while the y-axis remains unchanged. Blood glucose measures plotted on the graph may be connected by a single line; segments of the line may be color coded to indicate the corresponding day. This format facilitates recognition of trends in the data. In either one of the formats, it is envisioned that time may be assigned to the y-axis and the metric opposing time may be varied. It is noted that the range of acceptable blood glucose values may be demarcated with a visual indicator, such as shading.

The diabetes management application 200 and techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing"

or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

What is claimed is:

1. A computer-implemented method for displaying results of at least a three-day structured collection procedure of blood glucose measures obtained by a blood glucose meter to a user of a portable computing device, comprising administering, by the computing device, a structured collection procedure over a period of three days to the user, where the structured collection procedure specifies seven future events of pre-breakfast, post-breakfast, pre-lunch, post-lunch, pre-dinner, post-dinner, and bedtime and an acceptance window that is prospective for each of the plurality of future events for obtaining blood glucose measures from a patient throughout the course of a given day;

obtaining blood glucose measures from the patient by the user operating the blood glucose meter to perform the structured collection procedure over the period of three days;

transferring blood glucose measures from the blood glucose meter to the computing device by the user;

determining, by a sensor residing in the computing device, an orientation of a display of the computing device;

displaying, on a display of the computing device, a first graph for the structured collection procedure in response to a determination that a longitudinal axis of the display is orientated vertical, the first graph plots blood glucose measures from the seven predetermined events that meet the acceptance window that is prospective from each of the three days on the first graph such that one axis of the first graph represents time during a single day and blood glucose measures for each day is a time series represented by a separate line on the first graph; and displaying, on a display of the computing device, a second graph for the structured collection procedure in response to a determination that the longitudinal axis of the display is orientated horizontal, the second graph plots blood glucose measures from the seven predetermined events that meet the acceptance window that is prospective for each of the three days on the second graph such that one axis of the second graph represents time over three days and blood glucose measures are a time series represented by a single line on the second graph.

2. The method of claim 1 further comprises demarcating a range of acceptable blood glucose measures with visual indicia on at least one of the first graph and the second graph.

3. The method of claim 1 further comprises plotting blood glucose measures from different days with different visual indicia on at least one of the first graph and the second graph.

4. The method of claim 1 further comprises plotting blood glucose measures from different days with different colors on at least one of the first graph and the second graph.

5. The method of claim 1 wherein administering a structured collection procedure further includes receiving a data entry from the user of the computing device, where the data entry includes a blood glucose measure;

evaluating the data entry in relation to the structured collection procedure using a membership rule set, where the membership rule set defines rules for associating data entries with structured collection procedures; and associating the data entry with the structured collection procedure in accordance with a rule from the member rule set.

6. The method of claim 1 wherein administering a structured collection procedure further includes receiving a data entry from the user of the computing device, where the data entry includes a blood glucose measure;

evaluating the data entry in relation to the structured collection procedure using a membership rule set, where the membership rule set defines rules for associating data entries with structured collection procedures; and inputting the data entry into a logbook without an association to the structured collection procedure in accordance with a rule from the member rule set.

7. The method of claim 6 further comprises analyzing the data entry in relation to the plurality of predefined time slots for the structure collection procedure, wherein the membership rule set pertaining to the structured collection procedure of the second type includes a first rule that prohibits more than one collection event per time slot; and a second rule that requires each data entry associated with the structured collection procedure of the second type to match one of the predefined time slots.

8. A computer-implemented method for displaying results of an n-day patient profile to a user of a portable computing device, comprising administering, by the computing device, a structured collection procedure over a period of n days, where the structured collection procedure specifies a plurality of predefined time slots for obtaining blood glucose measures from a patient throughout the course of a given day;

obtaining, by the computing device, blood glucose measures from the patient during the administration of the structured collection procedure;

processing, by the computing device, the blood glucose measures as a time series in preparation for display;

determining, by a sensor in the computing device, an orientation of a display of the computing device with respect to horizon;

displaying, on a display of the computing device, a first graph for the structured collection procedure in response to a determination that a longitudinal axis of the display is orientated vertical, the first graph plots blood glucose measures from each of the n days on the first graph such that one axis of the first graph represents time during a single day and blood glucose measures for each day is represented by a separate line on the first graph; and displaying, on a display of the computing device, a second graph for the structured collection procedure in response to a determination that the longitudinal axis of the display is orientated horizontal, the second graph plots blood glucose measures for each of the n days as a single line along one axis of the second graph that represents time over the course of n days.

9. The method of claim 8 further comprises demarcating a range of acceptable blood glucose measures with visual indicia on at least one of the first graph and the second graph.

10. The method of claim 8 further comprises plotting blood glucose measures from different days with different visual indicia on at least one of the first graph and the second graph.

11. The method of claim 8 further comprises plotting blood glucose measures from different days with different colors on at least one of the first graph and the second graph.

12. The method of claim 8 wherein administering the structured collection procedure includes defining the plurality of predefined time slots from the group consisting of: before breakfast; after breakfast; before lunch; after lunch; before dinner; after dinner; and bedtime.

13. The method of claim 8 wherein administering a structured collection procedure further includes receiving a data entry from the user of the computing device, where the data entry includes a blood glucose measure;

evaluating the data entry in relation to the structured collection procedure using a membership rule set, where the membership rule set defines rules for associating data entries with structured collection procedures; and associating the data entry with the structured collection procedure in accordance with a rule from the member rule set.

14. The method of claim 8 wherein administering a structured collection procedure further includes receiving a data entry from the user of the computing device, where the data entry includes a blood glucose measure;

evaluating the data entry in relation to the structured collection procedure using a membership rule set, where the membership rule set defines rules for associating data entries with structured collection procedures; and inputting the data entry into a logbook without an association to the structured collection procedure in accordance with a rule from the member rule set.

15. The method of claim 14 further comprises analyzing the data entry in relation to the plurality of predefined time slots for the structure collection procedure, wherein the membership rule set pertaining to the structured collection procedure of the second type includes a first rule that prohibits more than one collection event per time slot; and a second rule that requires each data entry associated with the structured collection procedure of the second type to match one of the predefined time slots.

* * * * *